United States Patent
Sakaguchi et al.

(10) Patent No.: US 11,981,728 B2
(45) Date of Patent: May 14, 2024

(54) MONOCLONAL ANTIBODY, MEASUREMENT REAGENT FOR CYTOKERATIN 18 FRAGMENT, REAGENT KIT, AND MEASUREMENT METHOD

(71) Applicant: SYSMEX CORPORATION, Kobe (JP)

(72) Inventors: Kouji Sakaguchi, Kobe (JP); Naoya Okitsu, Kobe (JP); Minori Yamada, Kobe (JP); Naoko Kitamura, Kobe (JP); Tetsuji Yamaguchi, Kobe (JP)

(73) Assignee: SYSMEX CORPORATION, Kobe (JP)

(*) Notice: Subject to any disclaimer, the term of this patent is extended or adjusted under 35 U.S.C. 154(b) by 76 days.

(21) Appl. No.: 17/675,460

(22) Filed: Feb. 18, 2022

(65) Prior Publication Data

US 2022/0267427 A1 Aug. 25, 2022

(30) Foreign Application Priority Data

Feb. 22, 2021 (JP) .................................. 2021-026616

(51) Int. Cl.
*C07K 16/18* (2006.01)
(52) U.S. Cl.
CPC ........ *C07K 16/18* (2013.01); *C07K 2317/565* (2013.01)
(58) Field of Classification Search
None
See application file for complete search history.

(56) References Cited

U.S. PATENT DOCUMENTS

| | | | | |
|---|---|---|---|---|
| 6,180,370 B1* | 1/2001 | Queen | .................. | C07K 16/087 435/69.6 |
| 6,296,850 B1 | 10/2001 | Björklund et al. | | |
| 7,883,904 B2 | 2/2011 | Feldstein et al. | | |
| 2013/0260388 A1 | 10/2013 | Shen et al. | | |
| 2017/0192014 A1* | 7/2017 | Miller | .................. | C07K 16/18 |

FOREIGN PATENT DOCUMENTS

| | | | | |
|---|---|---|---|---|
| CN | 108265034 A | | 7/2018 | |
| EP | 337057 B1 | * | 4/1993 | ............. C07K 16/30 |
| WO | 2015/143277 A1 | | 9/2015 | |

OTHER PUBLICATIONS

Yamada, Minori, et al. Scientific Reports 11.1 (2021): 18187 (Year: 2021).*
Janeway, Charles A. "Immunobiology: The Immune System in Health and Disease." 2001 (Year: 2001).*
Kipriyanov, Sergey M., and Fabrice Le Gall. "Generation and production of engineered antibodies." Molecular biotechnology 26.1 (2004): 39-60. (Year: 2004).*
Y. Yilmaz: "Systematic review: caspase-cleaved fragments of cytokeratin 18—the promises and challenges of a biomarker for chronic liver disease", Alimentary Pharmacology & Therapeutics, 2009, vol. 30, Issue No. 11-12, pp. 1103-1109.
Extended European search report dated Jul. 15, 2022 in a counterpart European patent application No. 22157859.4.
"M30 Apoptosense® ELISA", Instructions for Use, PEVIVA, Sep. 28, 2018, 88 pages in total, VLVbio AB, Sweden.
Philippa M. O'Brien et al., "Antibody Phage Display: Methods and Protocols", Methods in Molecular Biology, 2002, 391 pages in total, vol. 178, Humana Press Inc., New Jersey, U.S.

* cited by examiner

*Primary Examiner* — Michael Szperka
*Assistant Examiner* — Lia E Taylor
(74) *Attorney, Agent, or Firm* — Sughrue Mion, PLLC

(57) ABSTRACT

Disclosed is an isolated monoclonal antibody comprising a heavy chain and a light chain, wherein the heavy chain comprises CDR1, CDR2 and CDR3 consisting of amino acid sequences set forth in SEQ ID NOs: 1, 2 and 3, respectively, and the light chain comprises CDR1, CDR2 and CDR3 consisting of amino acid sequences set forth in SEQ ID NOs: 4, 5 and 6, respectively.

4 Claims, 3 Drawing Sheets

Specification includes a Sequence Listing.

MONOCLONAL ANTIBODY, MEASUREMENT REAGENT FOR CYTOKERATIN 18 FRAGMENT, REAGENT KIT, AND MEASUREMENT METHOD

CROSS REFERENCE TO RELATED APPLICATIONS

This application claims priority from prior Japanese Patent Application No. 2021-026616, filed on Feb. 22, 2021, entitled "Monoclonal antibody, measurement reagent for cytokeratin 18 fragment, reagent kit and measurement method", the entire contents of which are incorporated herein by reference.

FIELD OF THE INVENTION

The present invention relates to a monoclonal antibody, a measurement reagent for cytokeratin 18 fragment, a reagent kit, and a measurement method.

BACKGROUND

Cytokeratin 18 (hereinafter referred to as "CK18") is cleaved by caspase in a process of apoptosis of epithelial cells such as hepatocytes, and becomes CK18 fragment (hereinafter referred to as "fCK18").

For example, fCK18 in the blood cleaved by caspase 3 is known as a biomarker reflecting diseases such as nonalcoholic steatohepatitis (hereinafter referred to as "NASH") in which apoptosis is induced and cancer. As a method for detecting fCK18, U.S. Pat. No. 6,296,850 is known. U.S. Pat. No. 6,296,850 discloses a monoclonal antibody that binds to a part of the C-terminus of fCK18 in order to detect fCK18.

SUMMARY OF THE INVENTION

The scope of the present invention is defined solely by the appended claims, and is not affected to any degree by the statements within this summary.

Provided is a novel isolated monoclonal antibody that binds to fCK18, which is an isolated monoclonal antibody including a heavy chain and a light chain, in which the heavy chain contains CDR1, CDR2 and CDR3 consisting of amino acid sequences set forth in SEQ ID NOs: 1, 2 and 3, respectively, and the light chain contains CDR1, CDR2 and CDR3 consisting of amino acid sequences set forth in SEQ ID NOs: 4, 5 and 6, respectively.

Provided is a reagent for measuring fCK18 containing the antibody, a reagent kit including the measurement reagent, and a method for measuring fCK18 using the antibody as a capture body or a detector.

DETAILED DESCRIPTION OF THE PREFERRED EMBODIMENTS

[1. Monoclonal Antibody]

Figure 1A:
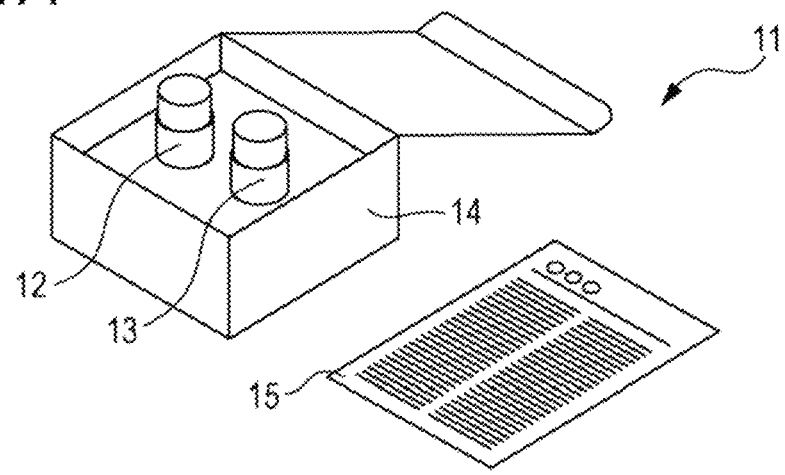
FIG. 1A is a schematic diagram showing an example of the reagent kit of the present embodiment.

The antibody of the present embodiment is an isolated monoclonal antibody including a heavy chain and a light chain, and has three complementarity determining regions (hereinafter referred to as "CDR") in each of variable regions of the heavy chain and the light chain. The three CDRs are called CDR1, CDR2 and CDR3, counting from the amino terminus of the antibody chain. The antibody of the present embodiment includes a CDR having the following amino acid sequence.

<Amino Acid Sequences of CDRs of Antibodies of Present Embodiment>

```
Heavy chain CDR1:
                                    (SEQ ID NO: 1)
SFGMH

Heavy chain CDR2:
                                    (SEQ ID NO: 2)
YISSGSTTIYYADTVKG Heavy chain CDR3:
                                    (SEQ ID NO: 3)
RGMITTGAWFAY Light chain CDR1:
                                    (SEQ ID NO: 4)
RASQRIGTSIH Light chain CDR2:
                                    (SEQ ID NO: 5)
YASESIS Light chain CDR3:
                                    (SEQ ID NO: 6)
QQSYIWPFT
```

The heavy chain of the antibody of the present embodiment preferably contains an amino acid sequence set forth in SEQ ID NO: 7. The light chain of the antibody of the present embodiment preferably contains an amino acid sequence set forth in SEQ ID NO: 8. The antibody according to one embodiment includes a heavy chain having the amino acid sequence set forth in SEQ ID NO: 7 and a light chain having the amino acid sequence set forth in SEQ ID NO: 8.

<Amino Acid Sequences of Variable Regions of Antibodies of Present Embodiment>

```
Variable region of heavy chain
                                    (SEQ ID NO: 7)
DVQLVESGGGLVQPGGSRKLSCAASGFTFSSFGMHWVRQAPEKGLEWVAYI

SSGSTTIYYADTVKGRFTISRDNPKNTLFLQMTSLRSEDTAMYYCARRGMI

TTGAWFAYWGQGTLVTVSA

Variable region of light chain
                                    (SEQ ID NO: 8)
DILLTQSPAILSVSPGERVSFSCRASQRIGTSIHWYQQRTNGSPRLLIKYA

SESISGIPSRFSGSGSGTDFTLSINSVESEDIADYYCQQSYIWPFTFGSGT

KLEIK
```

In the art, CDR sequences of the heavy chain and the light chain can be specified from a public database that determines the CDR sequence based on the amino acid sequence of the variable region of the antibody. Examples of such a database include VBASE2 (Reter I, Nucleic Acids Res. 2005). The CDR sequence of the antibody of the present embodiment is a sequence specified by VBASE2.

CK18 is one of intermediate filaments forming cytoskeleton of epithelial cells. As used herein, CK18 refers to human cytokeratin 18. The amino acid sequence of full-length CK18 (hereinafter referred to as "full length CK18") is set forth in an amino acid sequence of SEQ ID NO: 9. The full length CK18 is digested by an enzyme into fragments of various lengths. As the enzymatically digested fCK18, for example, the presence of fCK18 (1-239), fCK18 (239-430), and fCK18 (239-397) has been confirmed (Carlos, The Journal of cell biology 138.6 (1997): 1379-1394.). In the present specification, in SEQ ID NO: 9, fCK18 of the Xth to Yth amino acid sequences is represented as fCK18 (X-Y). Here, X and Y represent arbitrary natural numbers of 430 or less not including 0, and X represents a smaller number than Y. For example, fCK18 of the 239th to 397th amino acid sequences of SEQ ID NO: 9 is represented by fCK18 (239-397).

As shown in examples described later, in order for the antibody of the present embodiment to bind to an antigen, it is considered to be important that a C-terminal amino acid sequence of the antigen is an aspartic acid residue. Therefore, the antibody of the present embodiment shows binding to fCK18 (239-397) and fCK18 (261-397) among CK18, and shows substantially no binding to full length CK18 and fCK18 (239-396).

Here, the phrase "shows substantially no binding" includes not only does not bind at all but also shows binding to an extent that does not affect the measurement result in an immunoassay using the antibody of the present embodiment. For example, the phrase "shows substantially no binding" is binding 1/50 or less of the binding between the antibody of the present embodiment and fCK18 (381-397). The phrase "shows substantially no binding" is binding 1/100 or less in a more preferred example, and is binding 1/150 or less in a further preferred example. The binding between the antibody and the antigen can be measured by a method known in the art. Examples of such a method include immunoassay, immunoblotting, surface plasmon resonance analysis, and isothermal titration calorimetry analysis.

The antibody of the present embodiment may be a humanized antibody that has heavy chain CDR1, heavy chain CDR2, and heavy chain CDR3 consisting of amino acid sequences set forth in SEQ ID NOs: 1, 2, and 3, respectively, in a variable region of a heavy chain, and has light chain CDR1, light chain CDR2, and light chain CDR3 consisting of amino acid sequences set forth in SEQ ID NOs: 4, 5, and 6, respectively, in a variable region of a light chain. The humanized antibody is an antibody obtained by transplanting (CDR grafting) a gene sequence of CDR of a non-human-derived antibody into a human antibody gene. The antibody according to the present embodiment may be a chimeric antibody having a heavy chain variable region having the amino acid sequence set forth in SEQ ID NO: 7 and a light chain variable region having the amino acid sequence set forth in SEQ ID NO: 8. The chimeric antibody is an antibody in which a variable region and a constant region of an antibody derived from different species are linked.

Class of antibody of the present embodiment may be any of IgG, IgA, IgM, IgD and IgE, and is preferably IgG. A subclass of IgG is not particularly limited, and may be any of IgG1, IgG2, IgG3 and IgG4. As used herein, the "antibody" includes not only an immunoglobulin form but also an antibody fragment. Examples of such an antibody fragment include Fab, F(ab')2, Fab', Fv, Fd, domain antibody (dAb), single-chain antibody (scFv), and diabody.

The antibody of the present embodiment may be modified with a labeling substance known in the art. Such a labeling substance is not particularly limited as long as a detectable signal is generated. Examples of the labeling substance include a substance which itself generates a signal (hereinafter also referred to as "signal generating substance") and a substance which catalyzes a reaction of other substances to generate a signal. Examples of the signal generating substance include fluorescent substances, radioactive isotopes, and color developing substances. Examples of the substance which catalyzes a reaction of other substances to generate a detectable signal include enzymes. Examples of the fluorescent substances include fluorescent dyes such as fluorescein isothiocyanate (FITC), rhodamine and Alexa Fluor (registered trademark), and fluorescent proteins such as GFP. Examples of the radioactive isotopes include $^{125}$I, $^{14}$C, and $^{32}$P. Examples of the color developing substances include metal colloids such as gold nanocolloid. Examples of the enzyme include alkaline phosphatase, peroxidase, β-galactosidase, glucosidase, polyphenol oxidase, tyrosinase, acid phosphatase, and luciferase.

[2. Method for Producing Antibody]

The antibody of the present embodiment can be obtained by a known method for preparing a monoclonal antibody, such as a hybridoma method, a phage display method, or a genetic engineering method. When a hybridoma producing the antibody of the present embodiment is prepared by a hybridoma method, fCK18 can be used as an immunogen. Specifically, polypeptides shown in fCK18 (381-397) are exemplified. A method for synthesizing the polypeptide itself is known, and examples thereof include an Fmoc solid phase synthesis method. When immunogenicity of the synthesized polypeptide is low, the polypeptide is preferably bound to a carrier protein such as keyhole limpet hemocyanin (KLH) or albumin. When a carrier protein and a synthetic peptide are bound by crosslinking, it is preferable to add a cysteine residue to the N-terminus or C-terminus of the sequence when synthesizing the polypeptide. Alternatively, the immunogen can also be made as a recombinant protein. Recombinant fCK18 (X-397) (hereinafter also referred to as "rfCK18 (X-397)") can be obtained by incorporating a polynucleotide encoding an amino acid sequence of fCK18 (X-397) into a known expression vector, transforming a host cell with this vector to express rfCK18 (X-397), and then purifying by a known method.

Next, a mouse is immunized with the prepared polypeptide, and an antibody-producing cell such as a spleen cell is acquired from the immunized mouse. Then, according to the known method for preparing a hybridoma described in Kohler and Milstein, Nature, vol. 256, p. 495-497, 1975 and the like, the obtained antibody-producing cell is fused with an appropriate myeloma cell to obtain a hybridoma. For screening of hybridomas, a synthetic polypeptide used for immunogen can be used. The antibody of the present embodiment can be obtained from the culture supernatant of a hybridoma or ascites of a mammal intraperitoneally administered with the hybridoma. The obtained antibody may be purified by a known method such as salting out, affinity chromatography, or gel filtration.

When a hybridoma producing the antibody of the present embodiment is prepared, the hybridoma can be analyzed as described in Example 1 described later. Specifically, first, RNA extracted from the hybridoma is used to synthesize a polynucleotide encoding the antibody of the present embodiment, by a reverse transcription reaction and a RACE (rapid amplification of cDNA ends) method. Then, the base sequence of the synthesized polynucleotide is analyzed by sequencing, and the amino acid sequence of the antibody is determined based on the base sequence.

When the antibody of the present embodiment is prepared by a phage display method, for example, a Fab clone can be prepared. First, an animal such as a mouse is immunized with the synthetic polypeptide, mRNA is acquired from the spleen of the animal, and cDNA is synthesized. The obtained cDNA is amplified using a known primer for cloning an antibody gene to prepare a Fab phage library. Using the obtained library, a Fab clone of the antibody of the present embodiment can be obtained by a known Fab phage display method and biopanning (see Philippa M. O'Brien and Robert Aitken, Antibody Phage Display, (2002) Methods in Molecular Biology Volume No. 178).

When the antibody of the present embodiment is prepared by a genetic engineering method, examples thereof include a method using a host cell synthesis system and a cell-free protein synthesis system using artificial tRNA. When a host cell synthesis system is used, the antibody of the present embodiment can be prepared by using a vector containing an isolated polynucleotide encoding the antibody of the present embodiment and a host cell containing the vector. Specifically, a polynucleotide encoding the amino acid sequence of the antibody of the present embodiment can be incorporated into a known expression vector and a host cell is transformed with the vector to express the antibody of the present embodiment, followed by purification by a known method. The type of vector is not particularly limited. The vector can be appropriately selected from vectors known in the art such as expression vectors, cloning vectors, viral vectors, and the like. The type of the host cell is not particularly limited. The host cell can be appropriately selected from eukaryotic cells, prokaryotic cells, mammalian cells, and the like.

When a cell-free protein synthesis system is used, the protein can be synthesized by adding an amino acid, an energy molecule (for example, ATP, GTP, and the like), a polynucleotide encoding the amino acid sequence of the antibody of the present embodiment or the like to a cell extract containing a translation factor. As the cell extract containing a translation factor, for example, a cell extract of *E. coli*, yeast, rabbit reticulocyte, wheat germ, insect cell, mammalian culture cell or the like can be used.

[3. Reagent]

One embodiment of the present invention is a reagent for measuring fCK18. The reagent contains the antibody of the embodiment of [1. Monoclonal antibody] above. In the reagent of the present embodiment, fCK18 to be measured may be fCK18 detectable in the antibody, and is not particularly limited. Examples of such fCK18 include fCK18 (239-397), fCK18 (241-397), and fCK18 (261-397).

A form of the reagent of the present embodiment is not particularly limited, and may be solid (for example, powder, crystal, freeze-dried product, or the like) or liquid (for example, solution, suspension, emulsion, or the like). When the reagent is liquid, a solvent is not particularly limited as long as the antibody of the present embodiment can be stably stored. Examples of the solvent include water, physiological saline, phosphate buffered saline (PBS), tris buffered saline (TBS), Good's buffer, and combinations thereof. Examples of the Good's buffer include MES, Bis-Tris, ADA, PIPES, Bis-Tris-Propane, ACES, MOPS, MOPSO, BES, TES, HEPES, HEPPS, Tricine, Tris, Bicine, and TAPS.

The reagent of the present embodiment may contain known additives. Examples of the additive include protein stabilizers such as bovine serum albumin (BSA), preservatives such as sodium azide, inorganic salts such as sodium chloride, and combinations thereof

[4. Reagent Kit]

One embodiment of the present invention is a reagent kit for measuring fCK18. This reagent kit includes a reagent containing a capture body and a reagent containing a detector, and either the capture body or the detector contains the antibody described in [1. Monoclonal antibody]. The capture body preferably binds to a site different from a site to which the detector binds in fCK18.

In an embodiment, the capture body contains the antibody described in [1. Monoclonal antibody]. In this embodiment, the detector is not particularly limited as long as it can bind to fCK18, but it is preferable to bind to a site different from a site to which the capture body binds in fCK18. The detector may contain an antibody, an aptamer, and the like.

In another embodiment, the detector contains the antibody described in [1. Monoclonal antibody]. In this embodiment, the capture body is not particularly limited as long as it can bind to fCK18, but it is preferable to bind to a site different from a site to which the detector binds in fCK18. In this embodiment, the capture body preferably binds to fCK18 (239-397), and preferably binds to a site different from a site to which the detector binds in fCK18 (239-397). The capture body may contain an antibody, an aptamer, and the like. The detector may contain the antibody described in [1. Monoclonal antibody] as a primary antibody, a labeling substance, and a secondary antibody that binds to the primary antibody.

The reagent kit of the present embodiment may further include a solid phase for immobilizing the capture body. The solid phase may be any insoluble carrier capable of immobilizing the capture antibody. The mode of immobilization of the capture antibody on the solid phase is not particularly limited. For example, the capture antibody and the solid phase may be directly bound or indirectly bound via another substance. Examples of the direct binding include physical adsorption. Examples of the indirect binding include binding via a combination of biotins (including biotin and biotin analogs such as desthiobiotin) and avidins (including avidin and avidin analogs such as avidin streptavidin, and tamavidin (registered trademark)). In this case, by preliminarily modifying the capture antibody with biotins and previously binding avidins to the solid phase, the capture antibody and the solid phase can be indirectly bound via the bond between the biotins and the avidins.

The material of the solid phase is not particularly limited. For example, the material can be selected from organic polymer compounds, inorganic compounds, biopolymers, and the like. Examples of the organic polymer compound include latex, polystyrene, and polypropylene. Examples of the inorganic compound include magnetic bodies (iron oxide, chromium oxide, ferrite, and the like), silica, alumina, and glass. Examples of the biopolymer include insoluble agarose, insoluble dextran, gelatin, and cellulose. Two or more of these may be used in combination. The shape of the solid phase is not particularly limited, and examples thereof include microplates, microtubes, test tubes, particles, and membranes. Among them, microplates and particles (particularly, magnetic particles) are preferable.

In fCK18, the antibody that binds to a site different from a site to which the antibody binds described in [1. Monoclonal antibody] is not particularly limited, and for example, a commercially available antibody can be used. Examples thereof include trade name: M5 Keratin 18 Mab (clone name: M5, hereinafter referred to as "M5 antibody") (Diapharma), and trade name: M6 Keratin 18 Mab (clone name: M6, hereinafter referred to as "M6 antibody") (Diapharma).

The reagent kit of the present embodiment may further include a calibrator of fCK18. The fCK18 contained in the calibrator may be a recombinant or a synthetic peptide. As the fCK18 contained in the calibrator, for example, fCK18 (239-397), fCK18 (241-397), fCK18 (261-397) or the like can be used. When preparing a recombinant of the fCK18, recombinant fCK18 (261-397) is suitable from the viewpoint of expression efficiency.

Preferably, the calibrator of the present embodiment includes a plurality of reagents each containing fCK18, and the concentrations of fCK18 in the plurality of reagents are different from each one another. This calibrator may include, for example, a buffer solution containing no fCK18 (negative control) and a buffer solution containing fCK18 at a known concentration. The calibrator of one embodiment includes at least first to third containers, in which the first container contains a buffer solution containing no fCK18, the second container contains a first fCK18 solution, and the third container contains a second fCK18 solution. The fCK18 concentration of the first fCK18 solution and the fCK18 concentration of the second fCK18 solution of this embodiment are different.

The number of reagents contained in the calibrator included in the reagent kit of the present embodiment is not particularly limited, and can be selected from, for example, 2, 3, 4, 5, and 6 or more. The fCK18 concentration of the calibrator is not particularly limited as long as the concentration of fCK18 in a specimen can be determined based on the concentration.

A form of each reagent included in the reagent kit of the present embodiment is not particularly limited, and may be solid (for example, powder, crystal, freeze-dried product, or the like) or liquid (for example, solution, suspension, emulsion, or the like). When the reagent is liquid, a solvent is not particularly limited as long as the antibody of the present embodiment can be stably stored. Details of such a solvent are the same as those described in [3. Reagent].

Each reagent included in the reagent kit of the present embodiment may contain a known additive. Examples of the additive include protein stabilizers such as bovine serum albumin (BSA), preservatives such as sodium azide, and inorganic salts such as sodium chloride.

FIG. 1A shows an example of the reagent kit of the present embodiment. In FIG. 1A, 11 denotes a reagent kit, 12 denotes a first container containing a first reagent containing a capture body, 13 denotes a second container containing a reagent containing a detector, 14 denotes a packing box, and 15 denotes an attached document. Composition, usage, storage method and the like of each reagent may be described in the attached document. The reagent kit of this example may include other reagents. Examples of such a reagent include a solid phase for immobilizing the capture antibody, a buffer solution, and a calibrator.

Figure 1B:
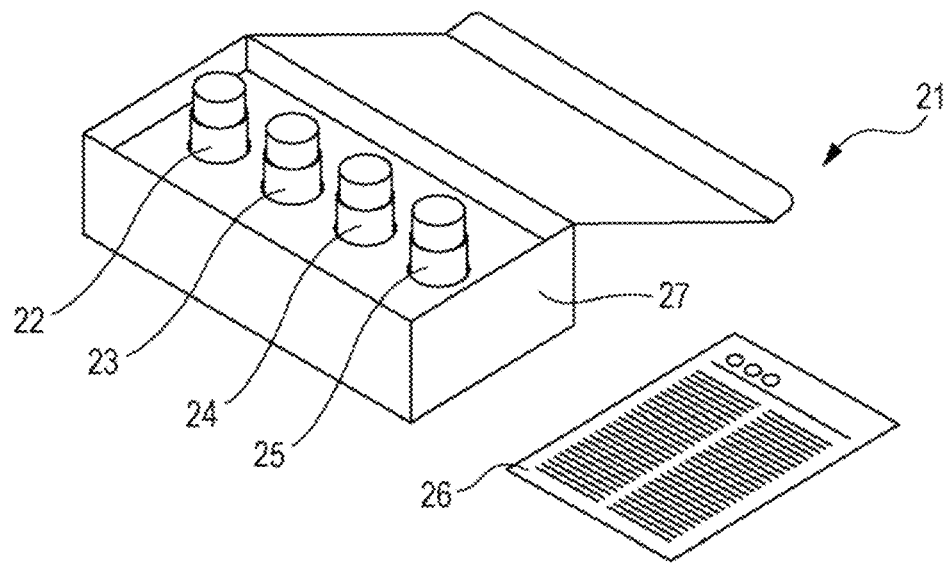
FIG. 1B is a schematic diagram showing an example of the reagent kit of the present embodiment.

FIG. 1B shows an example of the reagent kit of the embodiment. In FIG. 1B, 21 denotes a reagent kit, 22 denotes a first container containing a first reagent containing the antibody described in [1. Monoclonal antibody], 23 denotes a second container containing a reagent containing a detector, 24 and 25 denote a third container and a fourth container containing a calibrator reagent containing fCK18, and the fCK18 concentrations of the calibrator reagent contained in the third container 24 and the fourth container 25 are different from each other 26 denotes an attached document, and 27 denotes a packing box. The reagent kit of this example includes a first reagent containing the antibody described in [1. Monoclonal antibody], a reagent containing a detector, and a calibrator for quantification of fCK18, but may include other reagents. Examples of such a reagent include a solid phase for immobilizing the capture antibody, a buffer solution, and a calibrator reagent having an fCK18 concentration different from that of the above calibrator reagent.

[5. Method for Measuring fCK18]

One embodiment of the present invention is a method for measuring fCK18 in a specimen. This measurement method includes forming a complex containing a capture body, fCK18 in a specimen, and a detector (hereinafter also referred to as a "sandwich complex") on a solid phase, and measuring the fCK18 in the specimen based on the detector contained in the complex. Furthermore, the method is a method for measuring the fCK18 in the specimen in which the antibody contained in the capture body or the detector is the antibody described in [1. Monoclonal antibody].

The specimen of the present embodiment is a sample containing fCK18 or a sample suspected of containing fCK18. As the specimen, a sample derived from a living organism, a sample obtained by pretreating a sample derived from a living organism, a cell culture extract, a cell extract or the like can be used. Examples thereof include whole blood, serum, plasma, cerebrospinal fluid, semen, tissue, tissue fluid, and lymphatic fluid. When insoluble contaminants such as cells are contained in the specimen, impurities may be removed from the specimen by a known means such as centrifugal separation and filtration. The specimen may be diluted with an appropriate aqueous medium as necessary. Such an aqueous medium is not particularly limited as long as it does not interfere with the measurement described later, and examples thereof include water, physiological saline, and a buffer solution. The buffer solution is not particularly limited as long as it has a buffering effect at a pH near neutrality (for example, a pH of 6 or more and 8 or less). Examples of such buffer solution include Good's buffers such as HEPES, MES and PIPES, TBS, and PBS.

The measurement method of the present embodiment may include, in the forming, contacting the solid phase, the capture body, the fCK18 in the specimen, and the detector with one another. At this time, in the forming, the solid phase on which the capture body is previously immobilized, the fCK18 in the specimen, and the detector may be contacted with one another to form a complex on the solid phase.

In the contacting of the present embodiment, the order of contact among the solid phase, the capture body, the fCK18 and the detector is not particularly limited. In particular, it is preferable that the fCK18 and the capture body are contacted with each other to form a complex of a test substance in the specimen and the capture body, then the complex and the solid phase are contacted with each other to form a complex on the solid phase, and then the complex and the detector are contacted with each other to form a sandwich complex on the solid phase.

After forming the complex of the test substance and the capture body on the solid phase, it is preferable to perform B/F separation for removing unreacted components before contacting with the detector. The unreacted free component refers to a component not constituting a complex. Examples thereof include a capture antibody and a detection antibody not bound to fCK18. The means of B/F separation is not particularly limited, and when the solid phase is a particle, B/F separation can be performed by recovering only the solid phase capturing the complex by centrifugation. When the solid phase is a container such as a microplate or a microtube, B/F separation can be performed by removing a liquid containing an unreacted free component. When the solid phase is a magnetic particle, B/F separation can be performed by aspirating and removing a liquid containing an unreacted free component by a nozzle while magnetically constraining the magnetic particles with a magnet, which is preferable from the viewpoint of automation. After removing the unreacted free component, the solid phase capturing the complex may be washed with a suitable aqueous medium such as PBS.

The measured value of the fCK18 in the specimen can be acquired by detecting the complex formed on the solid phase by a method known in the art. For example, when an antibody labeled with a labeling substance is used as a detection antibody, the measured value of fCK18 can be acquired by detecting a signal generated by the labeling substance. Alternatively, also when a labeled secondary antibody against the detection antibody is used, the measured value of fCK18 can be acquired in the same manner.

The phrase "detecting a signal" herein includes qualitatively detecting the presence or absence of a signal, quantifying a signal intensity, and semi-quantitatively detecting the intensity of a signal. Semi-quantitative detection means to show the intensity of the signal in stages like "no signal generated", "weak", "medium", "strong", and the like. In the present embodiment, it is preferable to detect the intensity of a signal quantitatively or semi-quantitatively.

Methods for detecting a signal themselves are known in the art. In the present embodiment, a method according to the type of signal derived from the labeling substance may be appropriately selected. For example, when the labeling substance is an enzyme, signals such as light and color generated by reacting a substrate for the enzyme can be measured by using a known apparatus such as a spectrophotometer.

The substrate of the enzyme can be appropriately selected from known substrates according to the type of the enzyme. For example, when alkaline phosphatase is used as the enzyme, examples of the substrate include: chemiluminescent substrates such as CDP-Star (registered trademark) (disodium 4-chloro-3-(methoxyspiro[1,2-dioxetane-3,2'-(5'-chloro)tricyclo[3.3.1.13,7]decan]-4-yl)phenyl phosphate) and CSPD (registered trademark) (disodium 3-(4-methoxyspiro[1,2-dioxetane-3,2-(5'-chloro)tricyclo[3.3.1.13,7]decan]-4-yl)phenyl phosphate); and chromogenic substrates such as 5-bromo-4-chloro-3-indolyl phosphate (BCIP), disodium 5-bromo-6-chloro-indolyl phosphate and p-nitrophenyl phosphate. When peroxidase is used as the enzyme, examples of the substrate include chemiluminescent substrates such as luminol and derivatives thereof, and chromogenic substrates such as 2,2'-azinobis(3-ethylbenzothiazoline-6-ammonium sulfonate) (ABTS), 1,2-phenylenediamine (OPD) and 3,3',5,5'-tetramethylbenzidine (TMB).

When the labeling substance is a radioactive isotope, radiation as a signal can be measured using a known apparatus such as a scintillation counter. Also, when the labeling substance is a fluorescent substance, fluorescence as a signal can be measured using a known apparatus such as a fluorescence microplate reader. The excitation wavelength and the fluorescence wavelength can be appropriately determined according to the type of fluorescent substance used.

The detection result of the signal can be used as the measurement result of fCK18. For example, when quantitatively detecting the intensity of a signal, a measured value of the signal intensity itself or a value acquired from the measured value can be used as the measurement result of fCK18. Examples of the value acquired from the measured value of the signal intensity include a value obtained by subtracting the measured value of a negative control sample or the background value from the measured value. The measured value of the signal intensity may be applied to a calibration curve to determine the amount or concentration value of human fCK18. The negative control sample can be appropriately selected, and examples thereof include a biological sample obtained from a healthy subject.

The measurement method of the present embodiment may further include measuring, with the calibrator, the fCK18 concentration in the calibrator using the calibrator, and acquiring the concentration of fCK18 in the specimen based on the measured concentration.

In the measurement method of the present embodiment, the concentration of fCK18 in the specimen can be acquired from the measured value of fCK18 in the calibrator and the measured value of fCK18 in the specimen.

Since the concentration of fCK18 in the calibrator is known, the concentration of fCK18 in the specimen can be calculated from the measured value of fCK18 in the specimen based on the measured value of fCK18 in the calibrator. In a preferred embodiment, a calibration curve is prepared from the measured value of fCK18 in the calibrator, and the concentration of fCK18 in the specimen is calculated based on the calibration curve and the measured value of fCK18 in the specimen. The calibration curve can be prepared, for example, by plotting the measured values of the fCK18 in a plurality of calibrators on an XY plane in which the concentration of the fCK18 in the calibrator is taken on an X-axis and the measured values are taken on a Y-axis to obtain a straight line or a curve by a known method such as a least squares method. By applying the measured value of the fCK18 in the specimen to the prepared calibration curve, the concentration of the fCK18 in the specimen can be acquired.

In the present embodiment, the fCK18 in the specimen may be performed using a commercially available fully automated immunoassay system.

Examples of the fully automated immunoassay system include HISCL (trademark) series (Sysmex Corporation).

EXAMPLES

Hereinbelow, the present invention will be described in detail by examples, but the present invention is not limited to these examples.

Example 1

Acquisition of Antibody

[1] Acquisition of Hybridoma

Hybridomas producing antibody groups were obtained by mouse spleen method. Specifically, Peptide 1 (SEQ ID NO: 10) described in Table 1 was synthesized, this was conjugated with KLH, and an emulsion mixed with an adjuvant was immunized by injecting the emulsion into the abdominal cavity of Balb/C mouse five times and intravenously once. At this time, as the adjuvant, Freund's complete adjuvant was used for the first time, and Freund's incomplete adjuvant was used for the second and subsequent boosters. In addition, full-length recombinant CK18 (hereinafter also referred to as "full length rCK18") set forth in SEQ ID NO: 9 was used as an immunogen, and the immunogen was injected into the abdominal cavity four times and intravenously twice, in the same manner as described above for immunization. Three days after the final immunization, the spleen was removed from the mouse, and spleen cells were isolated from the spleen. Thereafter, the obtained spleen cells were subjected to cell fusion with mouse myeloma cells (P3-X63-Ag8.653) to obtain a hybridoma.

[2] Screening

From the hybridoma obtained in [1] above, reactivity with Peptide 1, Peptide 2 and full length rCK18 (manufactured by PROSPEC) described in Table 1 was measured by the following screening method (solid phase ELISA).

TABLE 1

| Peptide name | Amino acid sequence (N-terminus → C-terminus) | Sequence number |
| --- | --- | --- |
| Peptide 1 | RRILEDGEDFNLGDALD | 10 |
| Peptide 2 | RRLLEDGEDFNLGDAL | 11 |

<Screening method 1>
(1) An ANTI penta HIS antibody was added to an ELISA plate at 2.5 μg/mL and 50 μL/well, and the plate was allowed to stand at 4° C. overnight to immobilize the antibody. Thereafter, the plate was washed three times with PBST, and Buffer I' (10 mM $NaH_2PO_4.2H_2O$, 149.7 mM NaCl, 2.5 mM EDTA 2Na, 0.10% BSA, pH 7.0) was added thereto at 200 μL/well to prepare a plate stored at 4° C. overnight.
(2) Full length rCK18 was diluted with Buffer I' (10 mM $NaH_2PO_4.2H_2O$, 149.7 mM NaCl, 2.5 mM EDTA 2Na, 0.10% BSA, pH 7.0) so that the final concentration was 0.2 μg/mL to prepare an antigen diluent.
(3) The plate was washed three times with PBST, and each antigen diluent was added thereto at 50 μL/well, followed by shaking for 45 minutes.
(4) The plate was washed three times with PBST, and the culture supernatant was added thereto at 50 μL/well, followed by shaking for 45 minutes.
(5) The plate was washed three times with PBST, and 15000-fold diluted Peroxidase-conjugated Affinipure F(ab)'2 Fragment Goat Anti-Mouse IgG (H+L) (Jackson) was added thereto at 50 μL/well, followed by shaking for 45 minutes.
(6) The plate was washed three times with PBST, TMB Mix (1-step Ultra TMB-ELISA (Thermo Scientific):3% $H_2O_2$: Phosphate-Citrate buffer (Sigma)=15:0.15:14.85) was added thereto at 100 μL/well, and the mixture was reacted at room temperature for 10 minutes. Thereafter, 1 M $H_2SO_4$ was added thereto at 100 μL/well to stop the reaction.
(7) Absorbance of the reaction solution at 450 nm was measured with a plate reader.

<Screening Method 2>
(1) BSA was added to the N-terminus of Peptide 1 and Peptide 2.
(2) Each peptide was added to an ELISA plate at 5 μg/mL and 100 μL/well, and the plate was allowed to stand at 4° C. overnight to immobilize the peptide. Thereafter, the ELISA plate was washed three times with PBST, and Buffer I' (10 mM $NaH_2PO_4. 2H_2O$, 149.7 mM NaCl, 2.5 mM EDTA 2Na, 0.10% BSA, pH 7.0) was added thereto at 200 μL/well to prepare a plate stored at 4° C. overnight.
(3) The plate was washed three times with PBST, and the culture supernatant was added thereto at 100 μL/well, followed by shaking for 1 hour.
(4) The plate was washed three times with PBST, and 15000-fold diluted Peroxidase-conjugated Affinipure F(ab)'2 Fragment Goat Anti-Mouse IgG (H+L) (Jackson) was added thereto at 100 μL/well, followed by shaking for 1 hour.
(5) The plate was washed three times with PBST, TMB Mix (1-step Ultra TMB-ELISA (Thermo Scientific):3% $H_2O_2$: Phosphate-Citrate buffer (Sigma)=15:0.15:14.85) was added thereto at 100 μL/well, and the mixture was reacted at room temperature for 10 minutes. Thereafter, 1 M $H_2SO_4$ was added thereto at 100 μL/well to stop the reaction.
(6) Absorbance of the reaction solution at 450 nm was measured with a plate reader.

Four hybridomas producing antibodies reactive to full length rCK18 or Peptide 1 were selected.

[3] Epitope Analysis of Selected Antibodies

Reactivity of three antibodies (hereinafter referred to as "K18-91 antibody", "K18-287 antibody", and "K18-328 antibody") that are produced by hybridoma producing an antibody reactive to the full length rCK18 selected by screening with the synthetic peptides shown in Table 2 was measured by solid phase ELISA. In addition, reactivity of an antibody produced by a hybridoma producing an antibody reactive to Peptide 1 (hereinafter referred to as "K18-624 antibody") with Peptide 25, Peptide 26, and Peptide 27 was measured by solid phase ELISA.

<Method>
(1) The peptides shown in Table 2 were synthesized, and biotin was added to the N-terminal side.
(2) The synthesized peptides were dissolved in 80% DMSO solution and further diluted to 1 μg/ml with PBST.
(3) After washing an ELISA plate three times with PBST, a biotinylated peptide was added thereto at 100 μL/well, and the plate was allowed to stand at room temperature for 1 hour to immobilize the peptide. Thereafter, the plate was washed three times with PBST, and Buffer I' (10 mM $NaH_2PO_4.2H_2O$, 149.7 mM NaCl, 2.5 mM EDTA 2Na, 0.10% BSA, pH 7.0) was added thereto at 200 μL/well to prepare a plate stored at 4° C. overnight.
(4) The plate was washed three times with PBST, and an antibody diluted to 2 μg/ml was added thereto at 50 μL/well, followed by shaking at room temperature for 1 hour.
(5) The plate was washed three times with PBST, and an Anti-Mouse IgG POD antibody diluted about 5000 fold with Buffer I' (10 mM $NaH_2PO_4.2H_2O$, 149.7 mM NaCl, 2.5 mM EDTA 2Na, 0.10% BSA, pH 7.0) was added thereto at 50 μL/well, followed by shaking at room temperature for 1 hour.
(6) The plate was washed three times with PBST, TMB Mix (1-step Ultra TMB-ELISA (Thermo Scientific):3% $H_2O_2$: Phosphate-Citrate buffer (Sigma)=15:0.15:14.85) was added thereto at 100 μL/well, and the mixture was reacted at room temperature for 10 minutes. Thereafter, 1 M $H_2SO_4$ was added thereto at 100 μL/well to stop the reaction.
(7) Absorbance of the reaction solution at 450 nm was measured with a plate reader.

TABLE 2

| Peptide name | Amino acid sequence (N-terminus → C-terminus) | Sequence number |
|---|---|---|
| Peptide 3 | APKSQDLAKIMADIRAQY | 12 |
| Peptide 4 | LAKIMADIRAQYDELARK | 13 |
| Peptide 5 | DIRAQYDELARKNREELD | 14 |
| Peptide 6 | DELARKNREELDRYWSQQ | 15 |
| Peptide 7 | NREELDKYWSQQIEESTT | 16 |
| Peptide 8 | KYWSQQIEESTIVVTTQS | 17 |
| Peptide 9 | IEESTTVVTTQSAEVGAA | 18 |
| Peptide 10 | VVTTQSAEVGAAETTLTE | 19 |
| Peptide 11 | AEVGAAETTLTELRRTVQ | 20 |
| Peptide 12 | ETTLTELRRTVQSLEIDL | 21 |
| Peptide 13 | LRRTVQSLEIDLDSMRNL | 22 |
| Peptide 14 | SLEIDLDSMRNLKASLEN | 23 |
| Peptide 15 | DSMRNLKASLENSLREVE | 24 |
| Peptide 16 | KASLENSLREVEARYALQ | 25 |

TABLE 2-continued

| Peptide name | Amino acid sequence (N-terminus → C-terminus) | Sequence number |
|---|---|---|
| Peptide 17 | SLREVEARYALQMEQLNG | 26 |
| Peptide 18 | ARYALQMEQLNGILLHLE | 27 |
| Peptide 19 | MEQLNGILLHLESELAQT | 28 |
| Peptide 20 | ILLHLESELAQTRAEGQR | 29 |
| Peptide 21 | SELAQTRAEGQRQAQEYE | 30 |
| Peptide 22 | RAEGQRQAQEYEALLNIK | 31 |
| Peptide 23 | QAQEYEALLNIKVKLEAE | 32 |
| Peptide 24 | ALLNIKVKLEAEIATYRR | 33 |
| Peptide 25 | VKLEAEIATYRRLLEDGE | 34 |
| Peptide 26 | IATYRRLLEDGEDFNLGD | 35 |
| Peptide 27 | LLEDGEDFNLGDALD | 36 |

(Results)

The measurement results for the K18-91 antibody, the K18-287 antibody, and the K18-328 antibody are shown in Tables 3 to 5. The measurement results for the K18-624 antibody are shown in Table 6. The K18-91 antibody showed reactivity with Peptide 4. The K18-287 and K18-328 antibodies showed reactivity with Peptide 17. In addition, it was suggested that the K18-328 antibody has higher reactivity to Peptide 17 than the K18-287 antibody. The K18-624 antibody showed reactivity with Peptide 27.

TABLE 3

| Abs450\Peptide | 3 | 4 | 5 | 6 | 7 | 8 | 9 | 10 |
|---|---|---|---|---|---|---|---|---|
| K18-91 Antibody | 0.07 | 1.96 | 0.02 | 0.03 | 0.02 | 0.00 | 0.00 | 0.00 |
| K18-287 Antibody | 0.04 | 0.00 | -0.01 | 0.02 | 0.00 | 0.00 | -0.01 | 0.00 |
| K18-328 Antibody | 0.04 | 0.01 | -0.01 | 0.01 | 0.00 | -0.01 | -0.01 | 0.00 |

TABLE 4

| Abs450\Peptide | 11 | 12 | 13 | 14 | 15 | 16 | 17 | 18 |
|---|---|---|---|---|---|---|---|---|
| K18-91 Antibody | 0.02 | 0.03 | 0.02 | 0.00 | 0.00 | -0.01 | 0.02 | 0.02 |
| K18-287 Antibody | 0.00 | 0.00 | 0.00 | -0.01 | -0.02 | -0.04 | 1.05 | 0.01 |
| K18-328 Antibody | 0.01 | 0.00 | 0.01 | -0.01 | 0.00 | 0.04 | 1.55 | 0.02 |

TABLE 5

| Abs450\Peptide | 19 | 20 | 21 | 22 | 23 | 24 | 25 | 26 | 27 |
|---|---|---|---|---|---|---|---|---|---|
| K18-91 Antibody | 0.02 | 0.01 | 0.02 | 0.03 | 0.05 | 0.02 | 0.02 | 0.02 | 0.08 |
| K18-287 Antibody | 0.01 | 0.00 | 0.01 | 0.00 | 0.03 | 0.02 | 0.01 | 0.02 | 0.00 |
| K18-328 Antibody | 0.01 | 0.00 | 0.01 | 0.00 | 0.02 | 0.01 | 0.01 | 0.01 | 0.00 |

TABLE 6

| Abs450\Peptide | 25 | 26 | 27 |
|---|---|---|---|
| K18-624 Antibody | 0.14 | 0.14 | 2.34 |

[4] Analysis of Epitopes Using rCK18, rfCK18 and Peptides 1 and 2

Reactivity of the K18-328 antibody and the K18-624 antibody to the full length rCK18, a recombinant peptide consisting of 127th to 430th amino acid residues set forth in SEQ ID NO: 9 (hereinafter referred to as "rfCK18 (127-430)") (SEQ ID NO: 37) (Proteintech Inc.), and a recombinant peptide consisting of 239th to 396th amino acid residues set forth in SEQ ID NO: 9 (hereinafter referred to as "rfCK18 (239-396)") (SEQ ID NO: 38) (Cloud-Clone-Corp.) was measured by solid phase ELISA.

<Method>
(1) An ANTI GST antibody or a penta HIS antibody was added to an ELISA plat at 2.5 μg/mL and 50 μL/well, and the plate was allowed to stand at 4° C. overnight to immobilize the antibody. Thereafter, the plate was washed three times with PBST, and Buffer I' (10 mM NaH$_2$PO$_4$.2H$_2$O, 149.7 mM NaCl, 2.5 mM EDTA 2Na, 0.10% BSA, pH 7.0) was added thereto at 200 μL/well to prepare a plate stored at 4° C. overnight.
(2) Full length rCK18, rfCK18 (127-430) and rfCK18 (239-396) were each diluted with Buffer I' (10 mM NaH$_2$PO$_4$.2H$_2$O, 149.7 mM NaCl, 2.5 mM EDTA 2Na, 0.10% BSA, pH 7.0) so that the final concentration of the full length rCK18 was 0.2 μg/mL and the final concentrations of rfCK18 (127-430) and rfCK18 (239-396) were 0.3 µg/mL to prepare each antigen diluent.
(3) The plate was washed three times with PBST, and 50 µL each of each antigen diluent was added thereto, followed by shaking for 45 minutes.
(4) The K18-328 antibody solution and the K18-624 antibody solution were prepared to 5 to 10 ng/mL.
(5) The plate was washed three times with PBST, and a K18-328 antibody solution or a K18-624 antibody solution was added thereto at 50 µL/well, followed by shaking for 45 minutes.
(6) The plate was washed three times with PBST, and 15000-fold diluted Peroxidase-conjugated Affinipure F(ab)'2 Fragment Goat Anti-Mouse IgG (H+L) (Jackson) was added thereto at 50 µL/well, followed by shaking for 45 minutes.
(7) The plate was washed three times with PBST, TMB Mix (1-step Ultra TMB-ELISA (Thermo Scientific):3% $H_2O_2$: Phosphate-Citrate buffer (Sigma)=15:0.15:14.85) was added thereto at 100 µL/well, and the mixture was reacted at room temperature for 10 minutes. Thereafter, 1 M $H_2SO_4$ was added thereto at 100 µL/well to stop the reaction.
(8) Absorbance of the reaction solution at 450 nm was measured with a plate reader.

Subsequently, reactivity of the K18-328 antibody and the K18-624 antibody to Peptide 1 and Peptide 2 was measured by solid phase ELISA.
<Method>
(1) BSA was added to the N-terminus of Peptide 1 and Peptide 2.
(2) Each peptide was added to an ELISA plate at 5 µg/mL and 100 µL/well, and the plate was allowed to stand at 4° C. overnight to immobilize the peptide. Thereafter, the plate was washed three times with PBST, and Buffer I' (10 mM $NaH_2PO_4.2H_2O$, 149.7 mM NaCl, 2.5 mM EDTA 2Na, 0.10% BSA, pH 7.0) was added thereto at 200 µL/well to prepare a plate stored at 4° C. overnight.
(3) The K18-328 antibody solution and the K18-624 antibody solution were prepared to 5 to 10 ng/mL.
(4) The plate was washed three times with PBST, and a K18-328 antibody solution or a K18-624 antibody solution was added thereto at 100 µL/well, followed by shaking at room temperature for 1 hour.
(5) The plate was washed three times with PBST, and 15000-fold diluted Peroxidase-conjugated Affinipure F(ab)'2 Fragment Goat Anti-Mouse IgG (H+L) (Jackson) was added thereto at 100 µL/well, followed by shaking at room temperature for 1 hour.
(6) The plate was washed three times with PBST, TMB Mix (1-step Ultra TMB-ELISA (Thermo Scientific):3% $H_2O_2$: Phosphate-Citrate buffer (Sigma)=15:0.15:14.85) was added thereto at 100 µL/well, and the mixture was reacted at room temperature for 10 minutes. Thereafter, 1 M $H_2SO_4$ was added thereto at 100 µL/well to stop the reaction.
(7) Absorbance of the reaction solution at 450 nm was measured with a plate reader.

Finally, reactivity of the K18-328 antibody and the K18-624 antibody to a recombinant peptide comprising amino acid residues 239 to 397 set forth in SEQ ID NO: 9 (hereinafter referred to as "rfCK18 (239-397)") (SEQ ID NO: 39) was measured by combining immunoprecipitation and solid phase ELISA.
<Method>
(1) The K18-287 antibody was added to an ELISA plate at 5 µg/mL and 50 µL/well, and the plate was allowed to stand at 4° C. overnight to immobilize the peptide. Thereafter, the plate was washed three times with PBST, and Buffer I' (10 mM $NaH_2PO_4.2H_2O$, 149.7 mM NaCl, 2.5 mM EDTA 2Na, 0.10% BSA, pH 7.0) was added thereto at 200 µL/well to prepare a K18-287 antibody solid phase plate stored at 4° C. overnight.
(2) A biotinylated K18-91 antibody was prepared.
(3) 15% Anti-mouse IgG-conjugated sepharose 4B (CNBr-activated Sepharose 4B to which Goat, anti-Mouse IgG (H+L chain) was bound) was prepared.
(4) The K18-328 antibody solution and the K18-624 antibody solution were prepared to 1.25 µg/mL.
(5) rfCK18 (239-397) was prepared to 50 µg/mL. CHO cell culture supernatant was prepared.
(6) To a 96 well V-bottom plate were added the 15% anti-mouse IgG-binding sepharose 4B at 30 µL/well, the rfCK18 (239-397) at 30 µL/well, and the K18-328 antibody solution or the K18-624 antibody solution at 30 µL/well. In addition, one to which neither the K18-328 antibody solution nor the K18-624 antibody solution was added was prepared as a positive control, and one to which only the 15% anti-mouse IgG-binding sepharose 4B was added was prepared as a blank.
(7) The 96 well V-bottom plate was shaken at room temperature for 1 hour.
(8) The 96 well V-bottom plate was allowed to stand for 10 minutes to precipitate the anti-mouse IgG-binding sepharose 4B, then the supernatant of the 96 well V-bottom plate was added to the K18-287 antibody solid phase plate at 50 µL/well, followed by shaking at room temperature for 1 hour.
(9) A mixed solution of the biotinylated K18-91 antibody (final concentration: 2 µg/mL) and Streptavidin-POD conjugate (final concentration: 50 mU/mL) was prepared.
(10) The K18-287 antibody solid phase plate was washed three times with PBST, the mixed solution of the biotinylated K18-91 antibody and Streptavidin-POD conjugate was added at 50 µL/well, followed by shaking at room temperature for 1 hour.
(11) The K18-287 antibody solid phase plate was washed three times with PBST, TMB Mix (1-step Ultra TMB-ELISA (Thermo Scientific):3% $H_2O_2$: Phosphate-Citrate buffer (Sigma)=15:0.15:14.85) was added thereto at 100 µL/well, and the mixture was reacted at room temperature for 10 minutes. Thereafter, 1 M $H_2SO_4$ was added thereto at 100 µL/well to stop the reaction.
(12) Absorbance of the reaction solution at 450 nm was measured with a plate reader.
(13) Absorption rate (%) was calculated using the following formula.

Absorption rate (%)=(1−(Absorbance measured value of antibody sample liquid−Absorbance measured value of blank)/(Absorbance measured value of positive control−Absorbance measured value of blank))×100

(Results)

The measurement results are shown in Table 7. The K18-328 antibody showed binding to the full length rCK18, rfCK18 (127-430) and rfCK18 (239-396). All the proteins to which the K18-328 antibody showed binding contained Peptide 17. The K18-624 antibody showed no binding to the full length rCK18, rfCK18 (127-430), rfCK18 (239-396) and Peptide 2, and showed binding to Peptide 1 and rfCK18 (239-397). The C-terminal sequences of the proteins and peptides to which the K18-624 antibody did not show binding were not aspartic acid residues. On the other hand, the amino acid residues of the C-terminal residues of the proteins and peptides to which the K18-624 antibody showed binding were aspartic acid residues. From this result, it was considered that it is important that the C-terminal amino acid residues of the peptide and the protein be aspartic acid in order for the K18-624 antibody to bind.

TABLE 7

| Antibody | Abs450 | | | Absorption rate (%) | | |
|---|---|---|---|---|---|---|
| | Full length rCK18 | rfCK18 (127-430) | rfCK18 (239-396) | Peptide 1 | Peptide 2 | rfCK18 (239-397) |
| K18-328 Antibody | 0.516 | 0.890 | 0.525 | NT | NT | NT |
| K18-624 Antibody | NT | NT | 0.017 | 2.636 | 0.017 | 89.6 |

[5] Acquisition of Amino Acid Sequence and Identification of CDR Sequence

Amino acid sequences of the K18-328 antibody and the K18-624 antibody were acquired, and CDR sequences were identified.

<Method>

(1) Total RNA was prepared from hybridomas producing the K18-328 antibody and the K18-624 antibody.

(2) cDNA was synthesized using the prepared total RNA as a template.

(3) The cDNA was double-stranded with RNase H, and ligated with adapters.

(4) Using the obtained cDNA as a template, PCR was performed using a primer of constant region of H chain and an adapter primer, and a primer of constant region of L chain and an adapter primer to amplify a variable region.

(5) Amplified fragments of H chain and L chain were purified, and cloned into a cloning vector, then introduced into *E. coli* to obtain a transformant.

(6) A plasmid was prepared from the obtained transformant, and a base sequence and an amino acid sequence were acquired.

(7) CDR sequences were identified from the acquired base sequences using a public CDR sequence estimation database (VBASE2).

The CDR sequences identified based on the base sequence of the K18-328 antibody are shown in Table 8. The amino acid sequence of the variable region of the heavy chain of the K18-328 antibody was SEQ ID NO: 45, and the amino acid sequence of the variable region of the light chain was SEQ ID NO: 46. The CDR sequences identified based on the base sequence of the K18-624 antibody are shown in Table 9. The amino acid sequence of the variable region of the heavy chain of the K18-624 antibody was SEQ ID NO: 7, and the amino acid sequence of the variable region of the light chain was SEQ ID NO: 8.

TABLE 8

| K18-328 | Heavy chain (N-terminus → C-terminus) | Light chain (N-terminus → C-terminus) |
|---|---|---|
| CDR1 | GYTFTNYT (SEQ ID NO: 40) | ESVDSYGISF (SEQ ID NO: 43) |
| CDR2 | INPSSGYT (SEQ ID NO: 41) | AAS |
| CDR3 | ARQIPFAY (SEQ ID NO: 42) | QQSKEVPWT (SEQ ID NO: 44) |

TABLE 9

| K18-624 | Heavy chain (N-terminus → C-terminus) | Light chain (N-terminus → C-terminus) |
|---|---|---|
| CDR1 | SFGMH (SEQ ID NO: 1) | RASQRIGTSTH (SEQ ID NO: 4) |
| CDR2 | YISSGSTTIYYADTVKG (SEQ ID NO: 2) | YASESIS (SEQ ID NO: 5) |
| CDR3 | RGMITTGAWFAY (SEQ ID NO: 3) | QQSYIWPFT (SEQ ID NO: 6) |

Example 2

Comparison of Reactivity of K18-624 Antibody and M30 Antibody to Antigen

Reactivity of the K18-624 antibody acquired above and M30 antibody (U.S. Pat. No. 6,296,850) to the antigen was measured by immunoprecipitation and Western blotting.

<Method>

(1) Magnetic microbeads were sensitized with the K18-624 antibody and the M30 antibody (Diapharma) to prepare K18-624 antibody-bound magnetic microbeads and M30 antibody-bound magnetic microbeads, respectively.

(2) Apoptosis-induced HepG2 cell culture supernatant was diluted 2-fold, 10-fold, and 20-fold with a diluent (TBS, pH 7.5, 2% BSA) to prepare each sample solution.

(3) Each diluted sample solution and each of 0.5% antibody-bound magnetic microbeads were mixed, and then incubated (15 rpm, 4° C., O/N).

(4) The same operation was performed for each of 0.5% antibody-bound magnetic microbeads and a pool of healthy subjects.

(5) After washing the microbeads, an eluate (0.05% Rapi Gest) was added and incubated (67° C., 30 min), and the supernatant was subjected to Western blot analysis.

(6) After separation by polyacrylamide electrophoresis (SDS-PAGE), the supernatant was transferred to a PVDF membrane.

(7) The transferred PVDF membrane was blocked, and Fab of the K18-328 antibody prepared in Example 1 was incubated with an antibody labeled with alkaline phosphatase (K18-328Fab-ALP).

(8) Detection was performed by chemiluminescent reaction.

(Results)

Figure 2:
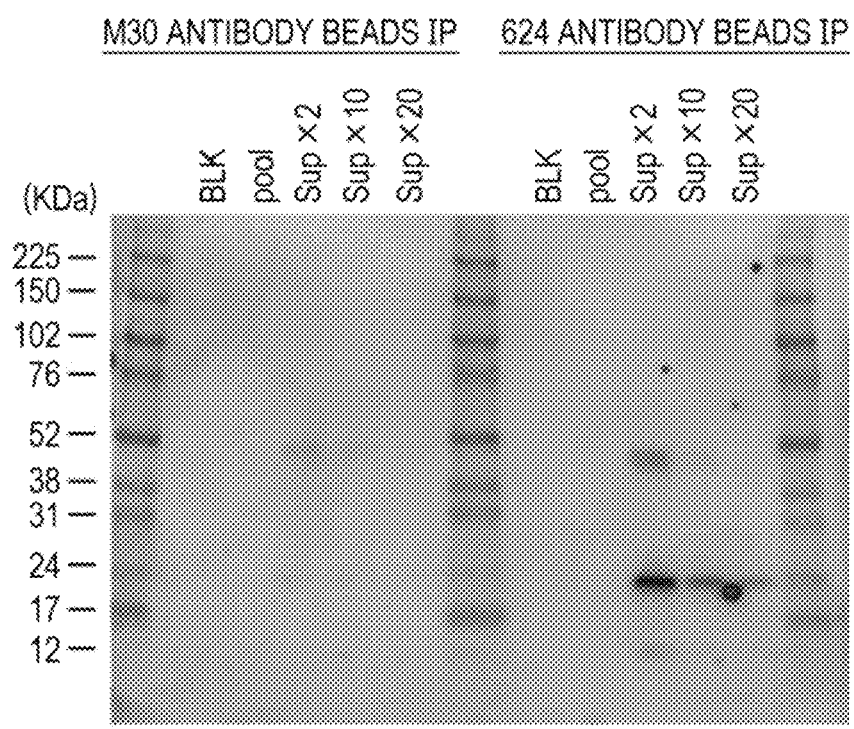
FIG. 2 shows results of IP-Western blotting of K18-624 antibody and M30 antibody of Example 2 with fCK18 (239-397)

The results of Example 2 are shown in FIG. 2. As to the M30 antibody described in U.S. Pat. No. 6,296,850, a band around 18 KDa was slightly observed in a lane to which 2-fold diluted cell supernatant was applied (FIG. 2, a lane indicated by M30 antibody microbeads IP, sup×2). On the other hand, as to the K18-624 antibody, a band around 18 KDa was observed in all lanes to which 2-fold, 10-fold, and 20-fold diluted cell supernatants were applied (FIG. 2, lanes indicated by K18-624 antibody microbead IP, sup×2, sup×10 and sup×20, respectively). It was suggested that the K18-

624 antibody had higher reactivity to fCK18 in apoptosis-inducing cells than the M30 antibody.

Example 3

Study of Expression of Calibrator Protein

A calibrator to be a standard substance of fCK18 was expressed using *E. coli*, and purification was performed. At that time, a JM109 strain (FUJIFILM Wako Pure Chemical Corporation) was used as a competent cell, and pBLC was used as a plasmid. A base sequence encoding 261st to 397th amino acids (SEQ ID NO: 47) of an amino acid sequence set forth in SEQ ID NO: 9 or a base sequence encoding 241st to 397th amino acids (SEQ ID NO: 48) of the amino acid sequence set forth in SEQ ID NO: 9 was ligated to pBLC (hereinafter, the prepared plasmids are referred to as "pBLC-fCK18 (261-397)" and "pBLC-fCK18 (241-397)", respectively).
<Method>
(1) The plasmid (pBLC-fCK18 (261-397) or pBLC-fCK18 (241-397)) was mixed into the competent cell and incubated on ice to obtain a transformant.
(2) After application to Lysogeny broth (LB) agar medium, the cells were cultured (37° C., O/N).
(3) A colony was inoculated into an LB liquid medium containing 100 µg/mL Ampicillin, and precultured (37° C., O/N, 300 rpm/min).
(4) The preculture solution was added to an LB medium containing 100 µg/mL Ampicillin, and cultured at 37° C., 200 rpm/min until OD660 changed from 0.5 to 0.6.
(5) Isopropyl β-D-thiogalactopyranoside (IPTG) was added to a final concentration of 0.5 mM, and the cells were cultured (37° C., O/N, 200 rpm/min).
(6) The culture solution was centrifuged (10,000 g, 4° C., 10 min), and then bacterial cells were washed and collected.
(7) The collected bacterial cells were resuspended in a buffer solution (Tris-buffered Saline (TBS), pH 7.5), sonicated, and then centrifuged to fractionate into a soluble fraction and an insoluble fraction.
(8) The soluble fraction obtained by disruption was subjected to affinity chromatography purification twice using an anti-fCK18 antibody binding column.
(9) The purified solution was subjected to a desalting column (trade name: PD-10, cytiva), and the solvent was replaced with TBS (pH 7.5).

Figure 3:
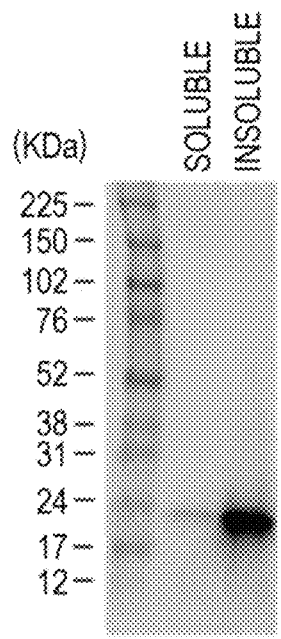
FIG. 3 shows results of Western blotting of soluble and insoluble fractions in purification step of recombinant fCK18 (241-397) of Example 3.
Figure 4:
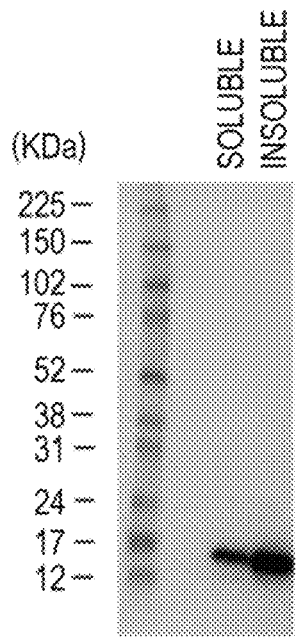
FIG. 4 shows results of Western blotting of soluble and insoluble fractions in purification step of recombinant fCK18 (261-397) of Example 3.

The results of performing Western blotting on the soluble and insoluble fractions of rfCK18 (241-397) are shown in FIG. 3. The results of performing Western blotting on the soluble and insoluble fractions of rfCK18 (261-397) are shown in FIG. 4. A band around 18 KDa of a lane to which the soluble fraction of rfCK18 (241-397) was applied (FIG. 3, a lane indicated by soluble) was clearer than a band around 16 KDa of a lane to which the soluble fraction of rfCK18 (261-397) was applied (FIG. 4, a lane indicated by soluble). This result suggested that when a recombinant protein was prepared using *E. coli* as a host, the expression level of the soluble fraction of rfCK18 (261-397) was higher than that of rfCK18 (241-397).

Example 4

(i) Measurement of fCK18 by Fully Automated Immunoassay System HISCL (Registered Trademark) (Sysmex Corporation) Using K18-624 Antibody Measurement samples of 3-fold dilution series (3-fold to 6561-fold dilution) were prepared from the apoptosis-induced HepG2 cell culture supernatant with a diluent (TBS, pH 7.5, 2% BSA), and fCK18 was measured. A calibration curve was prepared using the fCK18 (261-397) prepared in Example 3 as a calibrator. Based on the prepared calibration curve, fCK18 in the measurement sample was measured.

The fCK18 in the measurement sample was measured using HISCL (registered trademark). The measurement sample and HISCL (registered trademark) R1 to R3 reagents were set to the following solutions and volumes, and commercially available products were used as R4 reagent and R5 reagent (Sysmex Corporation). The measurement was performed by a two-step method according to the standard assay method of the attached document of the HISCL (registered trademark) reagent.
Measurement sample: 30 µL each
R1 reagent: 40 µL of diluent (TBS, pH 7.5, 2% BSA)
R2 reagent: 30 µL of 0.5% K18-624 antibody-bound magnetic microbeads liquid
R3 reagent: 100 of 0.1 µg/mL CK18 labeled antibody (K18-328Fab-ALP)
(ii) Measurement of fCK18 by ELISA Using K18-624 Antibody-Bound Magnetic Microbeads The measurement sample and the calibration curve were prepared in the same manner as in Example 4, and the fCK18 in the measurement sample was quantified by the following method.
<Method>
(1) 0.5% K18-624 Antibody-bound magnetic microbeads were diluted with a diluent (TBS, pH 7.5, 0.5% BSA) to prepare 0.05% K18-624 antibody-bound magnetic microbeads. This solution was added to an ELISA plate at 25 µL/well, then each measurement sample was added at 25 µL/well, and the plate was incubated (1500 rpm, RT, 20 min).
(2) After washing the plate, an anti-0.1 µg/mL CK18 labeled antibody (K18-328Fab-ALP) was added thereto at 25 µL/well, and the plate was incubated (1500 rpm, RT, 20 min).
(3) After washing the plate, the HISCL (registered trademark) R4 reagent was added thereto at 50 µL/well, and then the mixture was stirred (1500 rpm, RT, 1 min).
Thereafter, the HISCL (registered trademark) R5 reagent was added at 100 µL/well, and then the mixture was stirred (1000 rpm, RT, 10 sec).
(4) Luminescence intensity was measured with a plate reader.

Comparative Example 1

Measurement of fCK18 Using M30 Antibody

A measurement sample was prepared in the same manner as in Example 4. Using a commercially available fCK18 measuring kit (Diapharma), the fCK18 in the measurement sample was measured by the following method.
<Method>
(1) Each measurement sample was added to an ELISA plate at 25 µL/well, then M30 conjugate was added thereto at 75 µL/well, and the plate was incubated (600 prm, RT, 4 h).
(2) After washing the plate with Wash Buffer, TMB was added thereto at 200 µL/well, and the plate was incubated (Static shading, RT, 20 min).
(3) Stop Solution was added thereto at 50 µL/well, and after standing for 5 minutes, absorbance at 450 nm was measured.
(Results)

The results of calculating an S/N ratio based on the signal values measured in Example 4 and Comparative Example 1 are shown in Table 10. When the standard of sensitivity was set to an S/N ratio of 2 or more, fCK18 in apoptosis-inducing cells of 0.28 ng/mL or more in Example 4 (i), 0.09 ng/mL or more in Example 4 (ii), and 2.23 ng/mL or more in Comparative Example could be detected. Example 4 (i) had about 8-fold detection sensitivity compared with Comparative Example 1, and Example 4 (ii) had about 24-fold fCK18 detection sensitivity compared with Comparative Example 1. From the above, it was suggested that the K18-624 antibody can detect fCK18 with higher sensitivity than the M30 antibody.

TABLE 10

| fCK18 [ng/mL] | Example 4 (i) | Example 4 (ii) | Comparative Example 1 |
|---|---|---|---|
| 0 | — | — | — |
| 0.09 | 1.9 | 2.7 | 1.1 |
| 0.28 | 3.8 | 5.9 | 1.2 |
| 0.74 | 9.4 | 16.1 | 1.5 |
| 2.23 | 25.9 | 47.3 | 2.4 |
| 6.79 | 75.7 | 157.9 | 5.1 |
| 20.27 | 225.9 | 525.3 | 12.8 |
| 60.73 | 682.9 | 1848.4 | 37.5 |
| 182.28 | 2067.1 | 5564.2 | 48.3 |

Example 5

Measurement of fCK18 in Serum

For serum specimens collected from healthy subjects, the fCK18 concentration in a total of 20 specimens was measured. In addition, for serum specimens collected from NASH patients, the fCK18 concentration in a total of 14 specimens was measured. The measurement was performed by the same method and conditions as in Example 4.

The measurement results of the fCK18 concentration in the healthy subject specimens and the NASH patient specimens in Example 5 are shown in Table 11. As shown in Table 11, it was found that the fCK18 concentration in serum specimens collected from human can also be measured.

TABLE 11

| Healthy subject specimen | ng/mL | NASH Specimen | ng/mL |
|---|---|---|---|
| 1 | 1.17 | 1 | 1.95 |
| 2 | 0.19 | 2 | 5.51 |
| 3 | 0.08 | 3 | 5.22 |
| 4 | 0.17 | 4 | 7.15 |
| 5 | 0.31 | 5 | 15.53 |
| 6 | 0.19 | 6 | 5.92 |
| 7 | 0.20 | 7 | 4.53 |
| 8 | 0.22 | 8 | 5.70 |
| 9 | 0.37 | 9 | 4.32 |
| 10 | 3.09 | 10 | 6.14 |
| 11 | 0.08 | 11 | 2.98 |
| 12 | 2.34 | 12 | 3.26 |
| 13 | 0.28 | 13 | 4.37 |
| 14 | 2.19 | 14 | 11.07 |
| 15 | 0.28 | | |
| 16 | 0.42 | | |
| 17 | 0.32 | | |
| 18 | 0.77 | | |
| 19 | 0.45 | | |
| 20 | 2.50 | | |

Example 6

Measurement of Cancer Patient Specimen

For serum specimens collected from a plurality of cancer patients, the fCK18 concentration in 3 specimens of each cancer patient was measured. The measurement was performed by the same method and conditions as in Example 4.

The measurement results of the fCK18 concentration in the cancer patient specimens in Example 6 are shown in Table 12. As shown in Table 12, it was found that the fCK18 concentration in serum specimens collected from cancer patients can also be measured.

TABLE 12

| Cancer type | Number of specimens | Measurement range (ng/mL) |
|---|---|---|
| Stomach cancer | 3 | 0.77~1.66 |
| Colon cancer | 3 | 0.84~2.41 |
| Esophageal cancer | 3 | 0.25~1.60 |
| Bile duct cancer | 3 | 0.54~1.77 |
| Breast cancer | 3 | 0.53~16.46 |
| Lung cancer | 3 | 0.61~1.04 |
| Pancreatic cancer | 3 | 0.93~2.83 |

What is claimed is:

1. An isolated monoclonal antibody comprising a heavy chain and a light chain,
   wherein
   the heavy chain comprises CDR1, CDR2 and CDR3 consisting of amino acid sequences set forth in SEQ ID NOs: 1, 2 and 3, respectively, and
   the light chain comprises CDR1, CDR2 and CDR3 consisting of amino acid sequences set forth in SEQ ID NOs: 4, 5 and 6, respectively.

2. The monoclonal antibody according to claim 1, wherein the heavy chain comprises an amino acid sequence set forth in SEQ ID NO: 7, and the light chain comprises an amino acid sequence set forth in SEQ ID NO: 8.

3. The monoclonal antibody according to claim 1, wherein the monoclonal antibody binds to a peptide comprising an amino acid sequence set forth in SEQ ID NO: 10.

4. A reagent for measuring cytokeratin 18 fragment, comprising the monoclonal antibody according to claim 1.

* * * * *

SEQUENCE LISTING

```
<160> NUMBER OF SEQ ID NOS: 48

<210> SEQ ID NO 1
<211> LENGTH: 5
<212> TYPE: PRT
<213> ORGANISM: Mus musculus

<400> SEQUENCE: 1

Ser Phe Gly Met His
1               5

<210> SEQ ID NO 2
<211> LENGTH: 17
<212> TYPE: PRT
```

<213> ORGANISM: Mus musculus

<400> SEQUENCE: 2

Tyr Ile Ser Ser Gly Ser Thr Thr Ile Tyr Tyr Ala Asp Thr Val Lys
1               5                   10                  15

Gly

<210> SEQ ID NO 3
<211> LENGTH: 12
<212> TYPE: PRT
<213> ORGANISM: Mus musculus

<400> SEQUENCE: 3

Arg Gly Met Ile Thr Thr Gly Ala Trp Phe Ala Tyr
1               5                   10

<210> SEQ ID NO 4
<211> LENGTH: 11
<212> TYPE: PRT
<213> ORGANISM: Mus musculus

<400> SEQUENCE: 4

Arg Ala Ser Gln Arg Ile Gly Thr Ser Ile His
1               5                   10

<210> SEQ ID NO 5
<211> LENGTH: 7
<212> TYPE: PRT
<213> ORGANISM: Mus musculus

<400> SEQUENCE: 5

Tyr Ala Ser Glu Ser Ile Ser
1               5

<210> SEQ ID NO 6
<211> LENGTH: 9
<212> TYPE: PRT
<213> ORGANISM: Mus musculus

<400> SEQUENCE: 6

Gln Gln Ser Tyr Ile Trp Pro Phe Thr
1               5

<210> SEQ ID NO 7
<211> LENGTH: 121
<212> TYPE: PRT
<213> ORGANISM: Mus musculus

<400> SEQUENCE: 7

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
                20                  25                  30

Gly Met His Trp Val Arg Gln Ala Pro Glu Lys Gly Leu Glu Trp Val
            35                  40                  45

Ala Tyr Ile Ser Ser Gly Ser Thr Thr Ile Tyr Tyr Ala Asp Thr Val
        50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

-continued

Ala Arg Arg Gly Met Ile Thr Thr Gly Ala Trp Phe Ala Tyr Trp Gly
                100                 105                 110

Gln Gly Thr Leu Val Thr Val Ser Ala
        115                 120

<210> SEQ ID NO 8
<211> LENGTH: 107
<212> TYPE: PRT
<213> ORGANISM: Mus musculus

<400> SEQUENCE: 8

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Arg Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Tyr Ile Trp Pro Phe
                85                  90                  95

Thr Phe Gly Ser Gly Thr Lys Leu Glu Ile Lys
            100                 105

<210> SEQ ID NO 9
<211> LENGTH: 430
<212> TYPE: PRT
<213> ORGANISM: Homo sapiens

<400> SEQUENCE: 9

Met Ser Phe Thr Thr Arg Ser Thr Phe Ser Thr Asn Tyr Arg Ser Leu
1               5                   10                  15

Gly Ser Val Gln Ala Pro Ser Tyr Gly Ala Arg Pro Val Ser Ser Ala
            20                  25                  30

Ala Ser Val Tyr Ala Gly Ala Gly Gly Ser Gly Ser Arg Ile Ser Val
        35                  40                  45

Ser Arg Ser Thr Ser Phe Arg Gly Gly Met Gly Ser Gly Gly Leu Ala
    50                  55                  60

Thr Gly Ile Ala Gly Gly Leu Ala Gly Met Gly Gly Ile Gln Asn Glu
65                  70                  75                  80

Lys Glu Thr Met Gln Ser Leu Asn Asp Arg Leu Ala Ser Tyr Leu Asp
                85                  90                  95

Arg Val Arg Ser Leu Glu Thr Glu Asn Arg Arg Leu Glu Ser Lys Ile
            100                 105                 110

Arg Glu His Leu Glu Lys Lys Gly Pro Gln Val Arg Asp Trp Ser His
        115                 120                 125

Tyr Phe Lys Ile Ile Glu Asp Leu Arg Ala Gln Ile Phe Ala Asn Thr
    130                 135                 140

Val Asp Asn Ala Arg Ile Val Leu Gln Ile Asp Asn Ala Arg Leu Ala
145                 150                 155                 160

Ala Asp Asp Phe Arg Val Lys Tyr Glu Thr Glu Leu Ala Met Arg Gln
                165                 170                 175

Ser Val Glu Asn Asp Ile His Gly Leu Arg Lys Val Ile Asp Asp Thr
            180                 185                 190

```
Asn Ile Thr Arg Leu Gln Leu Glu Thr Glu Ile Glu Ala Leu Lys Glu
            195                 200                 205

Glu Leu Leu Phe Met Lys Lys Asn His Glu Glu Val Lys Gly Leu
210                 215                 220

Gln Ala Gln Ile Ala Ser Ser Gly Leu Thr Val Glu Val Asp Ala Pro
225                 230                 235                 240

Lys Ser Gln Asp Leu Ala Lys Ile Met Ala Asp Ile Arg Ala Gln Tyr
                245                 250                 255

Asp Glu Leu Ala Arg Lys Asn Arg Glu Glu Leu Asp Lys Tyr Trp Ser
            260                 265                 270

Gln Gln Ile Glu Glu Ser Thr Thr Val Val Thr Thr Gln Ser Ala Glu
        275                 280                 285

Val Gly Ala Ala Glu Thr Thr Leu Thr Glu Leu Arg Arg Thr Val Gln
290                 295                 300

Ser Leu Glu Ile Asp Leu Asp Ser Met Arg Asn Leu Lys Ala Ser Leu
305                 310                 315                 320

Glu Asn Ser Leu Arg Glu Val Glu Ala Arg Tyr Ala Leu Gln Met Glu
                325                 330                 335

Gln Leu Asn Gly Ile Leu Leu His Leu Glu Ser Glu Leu Ala Gln Thr
            340                 345                 350

Arg Ala Glu Gly Gln Arg Gln Ala Gln Glu Tyr Glu Ala Leu Leu Asn
        355                 360                 365

Ile Lys Val Lys Leu Glu Ala Glu Ile Ala Thr Tyr Arg Arg Leu Leu
370                 375                 380

Glu Asp Gly Glu Asp Phe Asn Leu Gly Asp Ala Leu Asp Ser Ser Asn
385                 390                 395                 400

Ser Met Gln Thr Ile Gln Lys Thr Thr Thr Arg Arg Ile Val Asp Gly
                405                 410                 415

Lys Val Val Ser Glu Thr Asn Asp Thr Lys Val Leu Arg His
            420                 425                 430

<210> SEQ ID NO 10
<211> LENGTH: 17
<212> TYPE: PRT
<213> ORGANISM: Artificial Sequence
<220> FEATURE:
<223> OTHER INFORMATION: synthetic

<400> SEQUENCE: 10

Arg Arg Leu Leu Glu Asp Gly Glu Asp Phe Asn Leu Gly Asp Ala Leu
1               5                   10                  15

Asp

<210> SEQ ID NO 11
<211> LENGTH: 16
<212> TYPE: PRT
<213> ORGANISM: Artificial Sequence
<220> FEATURE:
<223> OTHER INFORMATION: synthetic

<400> SEQUENCE: 11

Arg Arg Leu Leu Glu Asp Gly Glu Asp Phe Asn Leu Gly Asp Ala Leu
1               5                   10                  15

<210> SEQ ID NO 12
<211> LENGTH: 18
<212> TYPE: PRT
<213> ORGANISM: Artificial Sequence
<220> FEATURE:
```

```
<223> OTHER INFORMATION: synthetic

<400> SEQUENCE: 12

Ala Pro Lys Ser Gln Asp Leu Ala Lys Ile Met Ala Asp Ile Arg Ala
1               5                   10                  15

Gln Tyr

<210> SEQ ID NO 13
<211> LENGTH: 18
<212> TYPE: PRT
<213> ORGANISM: Artificial Sequence
<220> FEATURE:
<223> OTHER INFORMATION: synthetic

<400> SEQUENCE: 13

Leu Ala Lys Ile Met Ala Asp Ile Arg Ala Gln Tyr Asp Glu Leu Ala
1               5                   10                  15

Arg Lys

<210> SEQ ID NO 14
<211> LENGTH: 18
<212> TYPE: PRT
<213> ORGANISM: Artificial Sequence
<220> FEATURE:
<223> OTHER INFORMATION: synthetic

<400> SEQUENCE: 14

Asp Ile Arg Ala Gln Tyr Asp Glu Leu Ala Arg Lys Asn Arg Glu Glu
1               5                   10                  15

Leu Asp

<210> SEQ ID NO 15
<211> LENGTH: 18
<212> TYPE: PRT
<213> ORGANISM: Artificial Sequence
<220> FEATURE:
<223> OTHER INFORMATION: synthetic

<400> SEQUENCE: 15

Asp Glu Leu Ala Arg Lys Asn Arg Glu Glu Leu Asp Lys Tyr Trp Ser
1               5                   10                  15

Gln Gln

<210> SEQ ID NO 16
<211> LENGTH: 18
<212> TYPE: PRT
<213> ORGANISM: Artificial Sequence
<220> FEATURE:
<223> OTHER INFORMATION: synthetic

<400> SEQUENCE: 16

Asn Arg Glu Glu Leu Asp Lys Tyr Trp Ser Gln Gln Ile Glu Glu Ser
1               5                   10                  15

Thr Thr

<210> SEQ ID NO 17
<211> LENGTH: 18
<212> TYPE: PRT
<213> ORGANISM: Artificial Sequence
<220> FEATURE:
<223> OTHER INFORMATION: synthetic

<400> SEQUENCE: 17
```

```
Lys Tyr Trp Ser Gln Gln Ile Glu Glu Ser Thr Thr Val Val Thr Thr
1               5                   10                  15

Gln Ser
```

<210> SEQ ID NO 18
<211> LENGTH: 18
<212> TYPE: PRT
<213> ORGANISM: Artificial Sequence
<220> FEATURE:
<223> OTHER INFORMATION: synthetic

<400> SEQUENCE: 18

```
Ile Glu Glu Ser Thr Thr Val Val Thr Thr Gln Ser Ala Glu Val Gly
1               5                   10                  15

Ala Ala
```

<210> SEQ ID NO 19
<211> LENGTH: 18
<212> TYPE: PRT
<213> ORGANISM: Artificial Sequence
<220> FEATURE:
<223> OTHER INFORMATION: synthetic

<400> SEQUENCE: 19

```
Val Val Thr Thr Gln Ser Ala Glu Val Gly Ala Ala Glu Thr Thr Leu
1               5                   10                  15

Thr Glu
```

<210> SEQ ID NO 20
<211> LENGTH: 18
<212> TYPE: PRT
<213> ORGANISM: Artificial Sequence
<220> FEATURE:
<223> OTHER INFORMATION: synthetic

<400> SEQUENCE: 20

```
Ala Glu Val Gly Ala Ala Glu Thr Thr Leu Thr Glu Leu Arg Arg Thr
1               5                   10                  15

Val Gln
```

<210> SEQ ID NO 21
<211> LENGTH: 18
<212> TYPE: PRT
<213> ORGANISM: Artificial Sequence
<220> FEATURE:
<223> OTHER INFORMATION: synthetic

<400> SEQUENCE: 21

```
Glu Thr Thr Leu Thr Glu Leu Arg Arg Thr Val Gln Ser Leu Glu Ile
1               5                   10                  15

Asp Leu
```

<210> SEQ ID NO 22
<211> LENGTH: 18
<212> TYPE: PRT
<213> ORGANISM: Artificial Sequence
<220> FEATURE:
<223> OTHER INFORMATION: synthetic

<400> SEQUENCE: 22

```
Leu Arg Arg Thr Val Gln Ser Leu Glu Ile Asp Leu Asp Ser Met Arg
1               5                   10                  15

Asn Leu
```

<210> SEQ ID NO 23
<211> LENGTH: 18
<212> TYPE: PRT
<213> ORGANISM: Artificial Sequence
<220> FEATURE:
<223> OTHER INFORMATION: synthetic

<400> SEQUENCE: 23

Ser Leu Glu Ile Asp Leu Asp Ser Met Arg Asn Leu Lys Ala Ser Leu
1               5                   10                  15

Glu Asn

<210> SEQ ID NO 24
<211> LENGTH: 18
<212> TYPE: PRT
<213> ORGANISM: Artificial Sequence
<220> FEATURE:
<223> OTHER INFORMATION: synthetic

<400> SEQUENCE: 24

Asp Ser Met Arg Asn Leu Lys Ala Ser Leu Glu Asn Ser Leu Arg Glu
1               5                   10                  15

Val Glu

<210> SEQ ID NO 25
<211> LENGTH: 18
<212> TYPE: PRT
<213> ORGANISM: Artificial Sequence
<220> FEATURE:
<223> OTHER INFORMATION: synthetic

<400> SEQUENCE: 25

Lys Ala Ser Leu Glu Asn Ser Leu Arg Glu Val Glu Ala Arg Tyr Ala
1               5                   10                  15

Leu Gln

<210> SEQ ID NO 26
<211> LENGTH: 18
<212> TYPE: PRT
<213> ORGANISM: Artificial Sequence
<220> FEATURE:
<223> OTHER INFORMATION: synthetic

<400> SEQUENCE: 26

Ser Leu Arg Glu Val Glu Ala Arg Tyr Ala Leu Gln Met Glu Gln Leu
1               5                   10                  15

Asn Gly

<210> SEQ ID NO 27
<211> LENGTH: 18
<212> TYPE: PRT
<213> ORGANISM: Artificial Sequence
<220> FEATURE:
<223> OTHER INFORMATION: synthetic

<400> SEQUENCE: 27

Ala Arg Tyr Ala Leu Gln Met Glu Gln Leu Asn Gly Ile Leu Leu His
1               5                   10                  15

Leu Glu

<210> SEQ ID NO 28
<211> LENGTH: 18

```
<212> TYPE: PRT
<213> ORGANISM: Artificial Sequence
<220> FEATURE:
<223> OTHER INFORMATION: synthetic

<400> SEQUENCE: 28

Met Glu Gln Leu Asn Gly Ile Leu Leu His Leu Glu Ser Glu Leu Ala
1               5                   10                  15
Gln Thr

<210> SEQ ID NO 29
<211> LENGTH: 18
<212> TYPE: PRT
<213> ORGANISM: Artificial Sequence
<220> FEATURE:
<223> OTHER INFORMATION: synthetic

<400> SEQUENCE: 29

Ile Leu Leu His Leu Glu Ser Glu Leu Ala Gln Thr Arg Ala Glu Gly
1               5                   10                  15
Gln Arg

<210> SEQ ID NO 30
<211> LENGTH: 18
<212> TYPE: PRT
<213> ORGANISM: Artificial Sequence
<220> FEATURE:
<223> OTHER INFORMATION: synthetic

<400> SEQUENCE: 30

Ser Glu Leu Ala Gln Thr Arg Ala Glu Gly Gln Arg Gln Ala Gln Glu
1               5                   10                  15
Tyr Glu

<210> SEQ ID NO 31
<211> LENGTH: 18
<212> TYPE: PRT
<213> ORGANISM: Artificial Sequence
<220> FEATURE:
<223> OTHER INFORMATION: synthetic

<400> SEQUENCE: 31

Arg Ala Glu Gly Gln Arg Gln Ala Gln Glu Tyr Glu Ala Leu Leu Asn
1               5                   10                  15
Ile Lys

<210> SEQ ID NO 32
<211> LENGTH: 18
<212> TYPE: PRT
<213> ORGANISM: Artificial Sequence
<220> FEATURE:
<223> OTHER INFORMATION: synthetic

<400> SEQUENCE: 32

Gln Ala Gln Glu Tyr Glu Ala Leu Leu Asn Ile Lys Val Lys Leu Glu
1               5                   10                  15
Ala Glu

<210> SEQ ID NO 33
<211> LENGTH: 18
<212> TYPE: PRT
<213> ORGANISM: Artificial Sequence
<220> FEATURE:
<223> OTHER INFORMATION: synthetic
```

<400> SEQUENCE: 33

Ala Leu Leu Asn Ile Lys Val Lys Leu Glu Ala Glu Ile Ala Thr Tyr
1               5                   10                  15

Arg Arg

<210> SEQ ID NO 34
<211> LENGTH: 18
<212> TYPE: PRT
<213> ORGANISM: Artificial Sequence
<220> FEATURE:
<223> OTHER INFORMATION: synthetic

<400> SEQUENCE: 34

Val Lys Leu Glu Ala Glu Ile Ala Thr Tyr Arg Arg Leu Leu Glu Asp
1               5                   10                  15

Gly Glu

<210> SEQ ID NO 35
<211> LENGTH: 18
<212> TYPE: PRT
<213> ORGANISM: Artificial Sequence
<220> FEATURE:
<223> OTHER INFORMATION: synthetic

<400> SEQUENCE: 35

Ile Ala Thr Tyr Arg Arg Leu Leu Glu Asp Gly Glu Asp Phe Asn Leu
1               5                   10                  15

Gly Asp

<210> SEQ ID NO 36
<211> LENGTH: 15
<212> TYPE: PRT
<213> ORGANISM: Artificial Sequence
<220> FEATURE:
<223> OTHER INFORMATION: synthetic

<400> SEQUENCE: 36

Leu Leu Glu Asp Gly Glu Asp Phe Asn Leu Gly Asp Ala Leu Asp
1               5                   10                  15

<210> SEQ ID NO 37
<211> LENGTH: 304
<212> TYPE: PRT
<213> ORGANISM: Artificial Sequence
<220> FEATURE:
<223> OTHER INFORMATION: synthetic

<400> SEQUENCE: 37

Ser His Tyr Phe Lys Ile Ile Glu Asp Leu Arg Ala Gln Ile Phe Ala
1               5                   10                  15

Asn Thr Val Asp Asn Ala Arg Ile Val Leu Gln Ile Asp Asn Ala Arg
            20                  25                  30

Leu Ala Ala Asp Asp Phe Arg Val Lys Tyr Glu Thr Glu Leu Ala Met
        35                  40                  45

Arg Gln Ser Val Glu Asn Asp Ile His Gly Leu Arg Lys Val Ile Asp
    50                  55                  60

Asp Thr Asn Ile Thr Arg Leu Gln Leu Glu Thr Glu Ile Glu Ala Leu
65                  70                  75                  80

Lys Glu Glu Leu Leu Phe Met Lys Lys Asn His Glu Glu Glu Val Lys
                85                  90                  95

```
Gly Leu Gln Ala Gln Ile Ala Ser Ser Gly Leu Thr Val Glu Val Asp
                100                 105                 110
Ala Pro Lys Ser Gln Asp Leu Ala Lys Ile Met Ala Asp Ile Arg Ala
            115                 120                 125
Gln Tyr Asp Glu Leu Ala Arg Lys Asn Arg Glu Glu Leu Asp Lys Tyr
        130                 135                 140
Trp Ser Gln Gln Ile Glu Glu Ser Thr Thr Val Val Thr Thr Gln Ser
145                 150                 155                 160
Ala Glu Val Gly Ala Glu Thr Thr Leu Thr Glu Leu Arg Arg Thr
                165                 170                 175
Val Gln Ser Leu Glu Ile Asp Leu Asp Ser Met Arg Asn Leu Lys Ala
            180                 185                 190
Ser Leu Glu Asn Ser Leu Arg Glu Val Glu Ala Arg Tyr Ala Leu Gln
        195                 200                 205
Met Glu Gln Leu Asn Gly Ile Leu Leu His Leu Glu Ser Glu Leu Ala
    210                 215                 220
Gln Thr Arg Ala Glu Gly Gln Arg Gln Ala Gln Glu Tyr Glu Ala Leu
225                 230                 235                 240
Leu Asn Ile Lys Val Lys Leu Glu Ala Glu Ile Ala Thr Tyr Arg Arg
                245                 250                 255
Leu Leu Glu Asp Gly Glu Asp Phe Asn Leu Gly Asp Ala Leu Asp Ser
            260                 265                 270
Ser Asn Ser Met Gln Thr Ile Gln Lys Thr Thr Thr Arg Arg Ile Val
        275                 280                 285
Asp Gly Lys Val Val Ser Glu Thr Asn Asp Thr Lys Val Leu Arg His
    290                 295                 300

<210> SEQ ID NO 38
<211> LENGTH: 158
<212> TYPE: PRT
<213> ORGANISM: Artificial Sequence
<220> FEATURE:
<223> OTHER INFORMATION: synthetic

<400> SEQUENCE: 38

Ala Pro Lys Ser Gln Asp Leu Ala Lys Ile Met Ala Asp Ile Arg Ala
1               5                   10                  15
Gln Tyr Asp Glu Leu Ala Arg Lys Asn Arg Glu Glu Leu Asp Lys Tyr
            20                  25                  30
Trp Ser Gln Gln Ile Glu Glu Ser Thr Thr Val Val Thr Thr Gln Ser
        35                  40                  45
Ala Glu Val Gly Ala Glu Thr Thr Leu Thr Glu Leu Arg Arg Thr
    50                  55                  60
Val Gln Ser Leu Glu Ile Asp Leu Asp Ser Met Arg Asn Leu Lys Ala
65                  70                  75                  80
Ser Leu Glu Asn Ser Leu Arg Glu Val Glu Ala Arg Tyr Ala Leu Gln
                85                  90                  95
Met Glu Gln Leu Asn Gly Ile Leu Leu His Leu Glu Ser Glu Leu Ala
            100                 105                 110
Gln Thr Arg Ala Glu Gly Gln Arg Gln Ala Gln Glu Tyr Glu Ala Leu
        115                 120                 125
Leu Asn Ile Lys Val Lys Leu Glu Ala Glu Ile Ala Thr Tyr Arg Arg
    130                 135                 140
Leu Leu Glu Asp Gly Glu Asp Phe Asn Leu Gly Asp Ala Leu
145                 150                 155
```

<210> SEQ ID NO 39
<211> LENGTH: 159
<212> TYPE: PRT
<213> ORGANISM: Artificial Sequence
<220> FEATURE:
<223> OTHER INFORMATION: synthetic

<400> SEQUENCE: 39

Ala Pro Lys Ser Gln Asp Leu Ala Lys Ile Met Ala Asp Ile Arg Ala
1               5                   10                  15

Gln Tyr Asp Glu Leu Ala Arg Lys Asn Arg Glu Glu Leu Asp Lys Tyr
            20                  25                  30

Trp Ser Gln Gln Ile Glu Glu Ser Thr Thr Val Val Thr Thr Gln Ser
        35                  40                  45

Ala Glu Val Gly Ala Ala Glu Thr Thr Leu Thr Glu Leu Arg Arg Thr
    50                  55                  60

Val Gln Ser Leu Glu Ile Asp Leu Asp Ser Met Arg Asn Leu Lys Ala
65                  70                  75                  80

Ser Leu Glu Asn Ser Leu Arg Glu Val Glu Ala Arg Tyr Ala Leu Gln
                85                  90                  95

Met Glu Gln Leu Asn Gly Ile Leu Leu His Leu Glu Ser Glu Leu Ala
            100                 105                 110

Gln Thr Arg Ala Glu Gly Gln Arg Gln Ala Gln Glu Tyr Glu Ala Leu
        115                 120                 125

Leu Asn Ile Lys Val Lys Leu Glu Ala Glu Ile Ala Thr Tyr Arg Arg
    130                 135                 140

Leu Leu Glu Asp Gly Glu Asp Phe Asn Leu Gly Asp Ala Leu Asp
145                 150                 155

<210> SEQ ID NO 40
<211> LENGTH: 8
<212> TYPE: PRT
<213> ORGANISM: Mus musculus

<400> SEQUENCE: 40

Gly Tyr Thr Phe Thr Asn Tyr Thr
1               5

<210> SEQ ID NO 41
<211> LENGTH: 8
<212> TYPE: PRT
<213> ORGANISM: Mus musculus

<400> SEQUENCE: 41

Ile Asn Pro Ser Ser Gly Tyr Thr
1               5

<210> SEQ ID NO 42
<211> LENGTH: 8
<212> TYPE: PRT
<213> ORGANISM: Mus musculus

<400> SEQUENCE: 42

Ala Arg Gln Ile Pro Phe Ala Tyr
1               5

<210> SEQ ID NO 43
<211> LENGTH: 10
<212> TYPE: PRT
<213> ORGANISM: Mus musculus

<400> SEQUENCE: 43

Glu Ser Val Asp Ser Tyr Gly Ile Ser Phe
1               5                   10

<210> SEQ ID NO 44
<211> LENGTH: 9
<212> TYPE: PRT
<213> ORGANISM: Mus musculus

<400> SEQUENCE: 44

Gln Gln Ser Lys Glu Val Pro Trp Thr
1               5

<210> SEQ ID NO 45
<211> LENGTH: 115
<212> TYPE: PRT
<213> ORGANISM: Mus musculus

<400> SEQUENCE: 45

Gln Val His Leu Gln Gln Ser Ala Ala Glu Leu Ala Arg Pro Gly Ala
1               5                   10                  15

Ser Val Lys Met Ser Cys Lys Ala Ser Gly Tyr Thr Phe Thr Asn Tyr
                20                  25                  30

Thr Ile His Trp Ile Lys Gln Arg Pro Gly Gln Gly Leu Glu Trp Ile
            35                  40                  45

Gly Tyr Ile Asn Pro Ser Ser Gly Tyr Thr Asp Tyr Asn Gln Asn Phe
    50                  55                  60

Lys Asp Lys Thr Thr Leu Thr Ala Asp Lys Ser Ser Thr Thr Val Tyr
65                  70                  75                  80

Met Gln Leu Ser Ser Leu Thr Ser Glu Asp Ser Ala Val Tyr Tyr Cys
                85                  90                  95

Ala Arg Gln Ile Pro Phe Ala Tyr Trp Gly Gln Gly Thr Leu Val Thr
                100                 105                 110

Val Ser Ala
        115

<210> SEQ ID NO 46
<211> LENGTH: 111
<212> TYPE: PRT
<213> ORGANISM: Mus musculus

<400> SEQUENCE: 46

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
                20                  25                  30

Gly Ile Ser Phe Met Asn Trp Phe Gln Gln Lys Pro Gly Gln Pro Pro
            35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Val Asp Asp Thr Ala Met Tyr Phe Cys Gln Gln Ser Lys
                85                  90                  95

Glu Val Pro Trp Thr Phe Gly Gly Gly Thr Lys Leu Glu Ile Lys
                100                 105                 110

<210> SEQ ID NO 47

<211> LENGTH: 137
<212> TYPE: PRT
<213> ORGANISM: Artificial Sequence
<220> FEATURE:
<223> OTHER INFORMATION: synthetic

<400> SEQUENCE: 47

```
Arg Lys Asn Arg Glu Glu Leu Asp Lys Tyr Trp Ser Gln Gln Ile Glu
1               5                   10                  15
Glu Ser Thr Thr Val Val Thr Thr Gln Ser Ala Glu Val Gly Ala Ala
            20                  25                  30
Glu Thr Thr Leu Thr Glu Leu Arg Arg Thr Val Gln Ser Leu Glu Ile
        35                  40                  45
Asp Leu Asp Ser Met Arg Asn Leu Lys Ala Ser Leu Glu Asn Ser Leu
    50                  55                  60
Arg Glu Val Glu Ala Arg Tyr Ala Leu Gln Met Glu Gln Leu Asn Gly
65                  70                  75                  80
Ile Leu Leu His Leu Glu Ser Glu Leu Ala Gln Thr Arg Ala Glu Gly
                85                  90                  95
Gln Arg Gln Ala Gln Glu Tyr Glu Ala Leu Leu Asn Ile Lys Val Lys
            100                 105                 110
Leu Glu Ala Glu Ile Ala Thr Tyr Arg Arg Leu Leu Glu Asp Gly Glu
        115                 120                 125
Asp Phe Asn Leu Gly Asp Ala Leu Asp
    130                 135
```

<210> SEQ ID NO 48
<211> LENGTH: 157
<212> TYPE: PRT
<213> ORGANISM: Artificial Sequence
<220> FEATURE:
<223> OTHER INFORMATION: synthetic

<400> SEQUENCE: 48

```
Lys Ser Gln Asp Leu Ala Lys Ile Met Ala Asp Ile Arg Ala Gln Tyr
1               5                   10                  15
Asp Glu Leu Ala Arg Lys Asn Arg Glu Glu Leu Asp Lys Tyr Trp Ser
            20                  25                  30
Gln Gln Ile Glu Glu Ser Thr Thr Val Val Thr Thr Gln Ser Ala Glu
        35                  40                  45
Val Gly Ala Ala Glu Thr Thr Leu Thr Glu Leu Arg Arg Thr Val Gln
    50                  55                  60
Ser Leu Glu Ile Asp Leu Asp Ser Met Arg Asn Leu Lys Ala Ser Leu
65                  70                  75                  80
Glu Asn Ser Leu Arg Glu Val Glu Ala Arg Tyr Ala Leu Gln Met Glu
                85                  90                  95
Gln Leu Asn Gly Ile Leu Leu His Leu Glu Ser Glu Leu Ala Gln Thr
            100                 105                 110
Arg Ala Glu Gly Gln Arg Gln Ala Gln Glu Tyr Glu Ala Leu Leu Asn
        115                 120                 125
Ile Lys Val Lys Leu Glu Ala Glu Ile Ala Thr Tyr Arg Arg Leu Leu
    130                 135                 140
Glu Asp Gly Glu Asp Phe Asn Leu Gly Asp Ala Leu Asp
145                 150                 155
```